United States Patent
Shih

(10) Patent No.: US 9,873,152 B2
(45) Date of Patent: Jan. 23, 2018

(54) NANOPOROUS GOLD NANOPARTICLES AS HIGH-PAYLOAD MOLECULAR CARGOS, PHOTOTHERMAL/PHOTODYNAMIC THERAPEUTIC AGENTS, AND ULTRAHIGH SURFACE-TO-VOLUME PLASMONIC SENSORS

(71) Applicant: The University of Houston System, Houston, TX (US)

(72) Inventor: Wei-Chuan Shih, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 418 days.

(21) Appl. No.: 13/796,201

(22) Filed: Mar. 12, 2013

(65) Prior Publication Data
US 2014/0104606 A1 Apr. 17, 2014

Related U.S. Application Data

(60) Provisional application No. 61/609,451, filed on Mar. 12, 2012.

(51) Int. Cl.
| B22F 9/16 | (2006.01) |
| B22F 1/00 | (2006.01) |
| G01N 21/65 | (2006.01) |

(52) U.S. Cl.
CPC .............. *B22F 9/16* (2013.01); *B22F 1/0044* (2013.01); *G01N 21/658* (2013.01)

(58) Field of Classification Search
CPC .. G01N 21/554; G01N 21/658; B22F 1/0044; B82Y 30/00
See application file for complete search history.

(56) References Cited

U.S. PATENT DOCUMENTS

| 6,970,239 B2 * | 11/2005 | Chan et al. .................... 356/301 |
| 7,428,046 B2 * | 9/2008 | Wang et al. ................... 356/301 |
| 2002/0146745 A1 * | 10/2002 | Natan ................... G01N 33/538 |
| | | 435/7.1 |
| 2004/0161369 A1 * | 8/2004 | Chan et al. ................ 422/82.05 |
| 2005/0282229 A1 * | 12/2005 | Su ..................... G01N 33/48721 |
| | | 435/7.1 |

(Continued)

FOREIGN PATENT DOCUMENTS

WO WO2012/058154 A2 * 5/2012 ............. B01D 39/14

OTHER PUBLICATIONS

Qiuming Yu, "Inverted Size-Dependence of Surface-Enhanced Raman Scattering on Gold Nanohole and Nanodisk arrays", Nano Letters, 2008.*

(Continued)

*Primary Examiner* — Michael A Lyons
*Assistant Examiner* — Maurice Smith
(74) *Attorney, Agent, or Firm* — Jackson Walker LLP

(57) ABSTRACT

A nanoporous gold disk (NPGD) as a novel surface-enhanced Raman spectroscopy (SERS) substrate. NPGD has SERS enhancement factor similar to that of gold nanoshells, but allows, for example, at least three times more benzenethiol molecules to be attached to its surface due to large surface-to-volume ratio. The high capacity enables the rapid detection of attomole-level benzenethiol molecules with relatively high detector temperatures. Additionally, a fabrication process to make NPGD with controlled size and highly reproducible SERS activities.

13 Claims, 30 Drawing Sheets

(56) References Cited

U.S. PATENT DOCUMENTS

| | | |
|---|---|---|
| 2006/0034729 A1* | 2/2006 | Poponin .................... 422/82.05 |
| 2006/0061762 A1* | 3/2006 | Dwight et al. ................ 356/301 |
| 2010/0087723 A1 | 4/2010 | Vann Duyne et al. |
| 2010/0323518 A1 | 12/2010 | Oppermann et al. |
| 2011/0014300 A1 | 1/2011 | Muthusamy et al. |

OTHER PUBLICATIONS

Chan et al. "Plasnnonic Properties of Copper Nanoparticles Fabricated by Nanosphere Lithography" Nano Letters, Jun. 13, 2007, vol. 7 pp. 1947-1951.

* cited by examiner

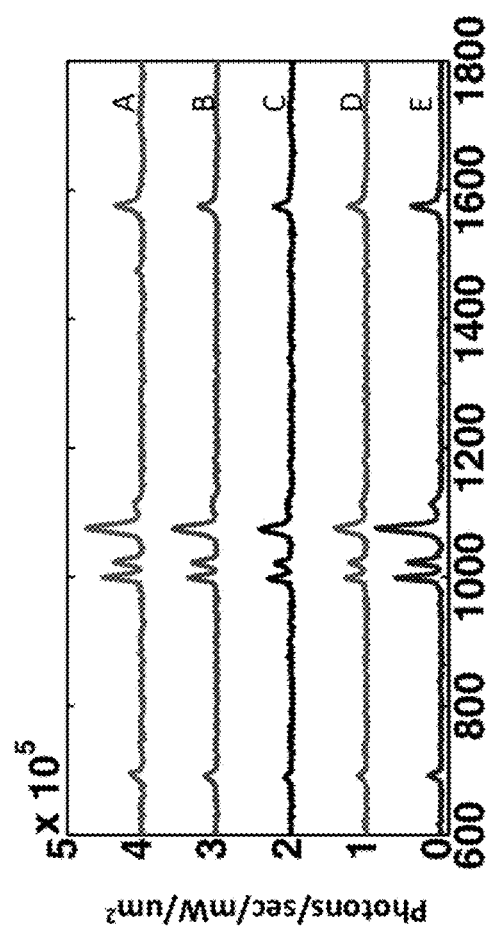
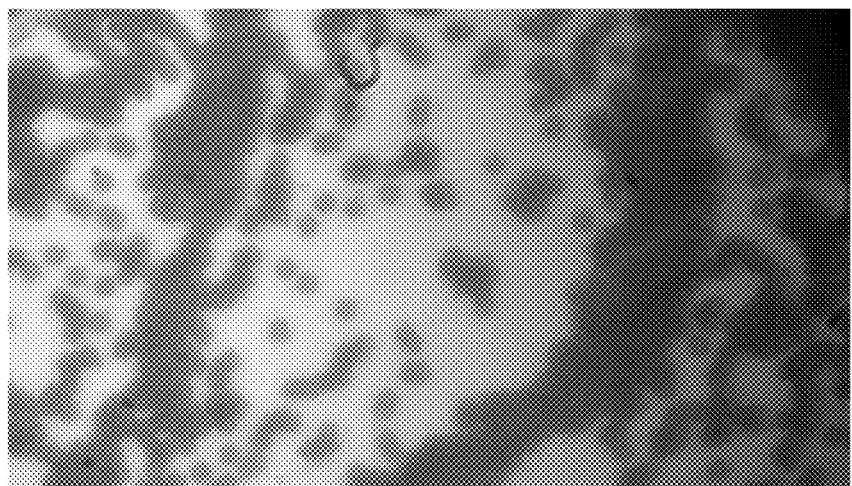
Fig. 14(c)
Fig. 14(d)

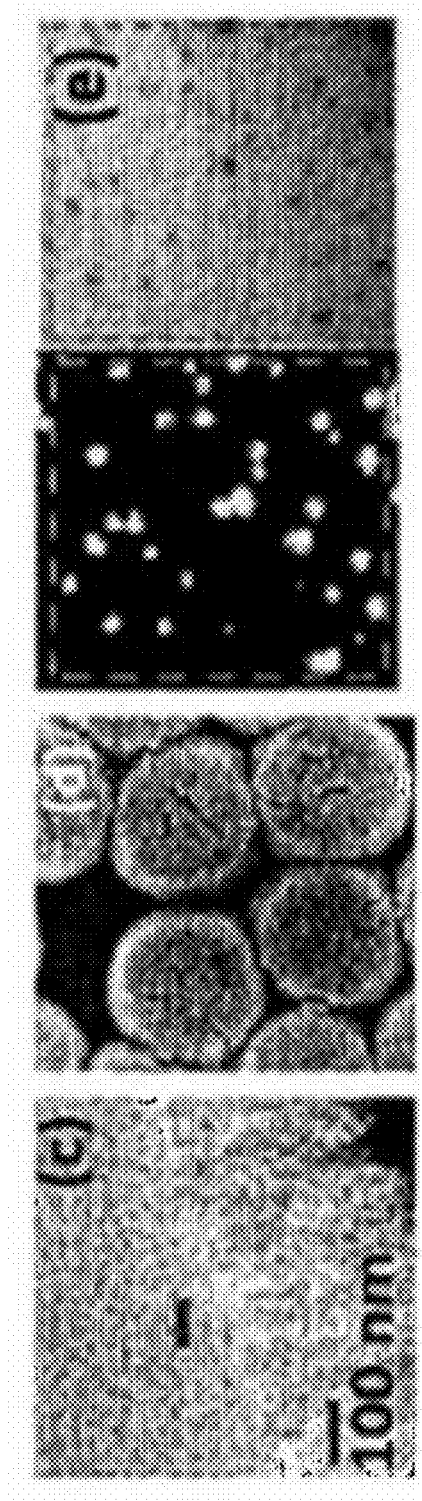

NANOPOROUS GOLD NANOPARTICLES AS HIGH-PAYLOAD MOLECULAR CARGOS, PHOTOTHERMAL/PHOTODYNAMIC THERAPEUTIC AGENTS, AND ULTRAHIGH SURFACE-TO-VOLUME PLASMONIC SENSORS

RELATED APPLICATIONS

This application claims priority to U.S. Provisional Patent Application No. 61/609,451 filed Mar. 12, 2012, which is hereby incorporated by reference for all purposes.

FIELD

The present disclosure relates generally to nanoporous materials. More specifically, this disclosure relates to nanoporous gold nanoparticles (NPGNs).

BACKGROUND

A single living cell is a dynamic system constantly sensing and reacting to external stimuli, and can already be considered as a biological network itself. As the hierarchy upgrades, many cells can form a more complex biological network and demonstrate communication and collective behavior. To unravel the biological network even at the single cell level is still challenging because of its complexity and is a critical subject in fields such as system biology. One of the most important tricks in all experimental science is to effectively vary only one thing at a time. As such, the spatial and temporal precision of the delivery of controlled changes is critical.

Recently, we have witnessed a paradigm shift from extracellular control of environmental stimuli to intracellular control of the actual internal connections themselves, which can potentially provide new insights of the living cellular machinery. As an obvious example, an external stimulus will most likely trigger a cascade of cell signaling via various pathways before its effect is actually received by the intended intracellular party. The response of interest may be completely masked or misinterpreted due to signal loss, attenuation or distortion within the long string of signaling cascade. Therefore, intracellular techniques have the potential to deliver the controlled effectors with much improved spatial, temporal and even molecular precision.

Recent advances in nanoplasmonic technology have enabled new tools for light-gated drug delivery, photothermal therapy, DNA release, inducing protein aggregates, and nanometer scale direct interfacing with intracellular processes using oligonucleotides. A distinct advantage of gold nanoparticle-based approaches compared to lysosome vesicle or other metals is the much better control in coating, or functionalizing, them with thiolated ligands directly or through linker molecules, and its chemical inertness. Colloidal gold nanosphere has been first used as a photothermal agent for therapies and light-gated release of surface coated molecules. With plasmon resonance near 540 nm, in vivo applications were limited however by the strong scattering and absorption of skin, tissue, and hemoglobin at this wavelength. As a result, various colloidal gold nanoparticles of other geometry have been developed, e.g., nanoshell, nanorod, and nanocage, with two primary goals: shifting the resonance into the near-infrared transmission window and increasing the nanoparticle's cargo capacity.

Plasmonic nanoparticles are generally characterized by scanning electron microcopy or dynamic light scattering for size distribution, absorption spectroscopy for both size and plasmonic resonance, and surface-sensitive techniques such as surface-enhanced Raman spectroscopy (SERS) using surface adsorbate or thiolated hydrocarbon as markers. Among these, SERS provides label-free adsorbate identification with the highest nanoparticle-molecule distance sensitivity because only the molecules within a few nanometers of the gold surface can be enhanced. In addition, SERS is arguably the most robust and sensitive technique for real biological applications because it is a background-free measurement assuming the photoluminescence from other interferents is negligible.

Over the past decade, many types of colloidal nanoparticles of various shapes have been developed as shown and described below. All the existing nanoparticles share the same feature, that is, they are solid-core, with nanocage as the only exception, which features an empty void inside a "porous" box. Therefore, only a small fraction, i.e., the molecules absorbed on nanocage walls, could be plasmonically enhanced, rendering single nanocage undetectable by SERS.

SUMMARY

Surface-enhanced Raman spectroscopy has been widely used for high-sensitivity molecular detection and identification. However, as for most surface sensors, the performance of a SERS sensor is usually controlled by the delivery and binding of molecular analytes to the sensing surface. To address this challenge, we disclose a novel monolithic plasmonic nanofluidic architecture that exploits a 3-dimensional sensing volume inside nanoporous gold (NPG), as shown in FIG. 1(a). Unlike conventional sensors that only utilize an approximately flat sensing surface, our approach features an ultrahigh surface-to-volume ratio for collecting a large number of molecules inside the sensing volume that is matched to the optical focal volume. Further, once entering the sensing volume, these molecules are immersed in a plasmonic field that retains them and enables SERS acquisition over a prolonged period of time. The analytes can be released from the sensing volume after being measured by simply turning off the laser, and new analytes can be flowed in, trapped by the plasmonic field, and measured in a batch fashion, thereby enabling continuous monitoring. We envision that this approach will provide a powerful trapping mechanism to complement current surface binding strategies based on chemical or biochemical functionalization of the sensor surface. Moreover, this approach can become a versatile label- and surface functionalization-free technique for highly multiplexed sensing. Further, the proposed platform provides a unique opportunity to simultaneously exploit and study the synergy between nanofluidic confinement, plasmonic trapping and field enhancement.

We disclose a novel class of nanoparticle, dubbed nanoporous gold nanoparticle (NPGN). As shown the figures and described below, NPGNs feature a fine porous network with pore size ~20 nm in some embodiments throughout its entire volume, which is not seen in any existing gold nanoparticles including solid- or hollow-core nanosphere, nanorod, nanoshell, nanocrescent, and nanocage. The external shape of our first NPGN is similar to a nanodisk with a diameter of ~400-500 nm and a thickness of ~75 nm. Both the diameter and thickness can be easily tuned by slightly changing fabrication parameters. The high porosity is intriguing and critically important in several aspects.

First, the increased surface area would permit NPGN to carry a much higher payload of surface adsorbates. This feature has significant implication in nanoparticle-based molecular cargo for the delivery of drugs, proteins, DNA and RNA into cells. It has a significant potential in improving current cancer treatment via chemotherapy, radiation therapy, or the combination of the two. Second, the NPGN is "semitransparent" due to its porous nature. Thus, the internal surface adsorbates may in some cases be optically measured. In other words, the amount of internal payload can be quantified via optical methods. Third, with proper surface linkage, the entire 3-dimensional internal volume can be "filled" and thus payload may be further increased without paying the price of size increase. Fourth, due to the fine pore structures, the majority of the "filler" or surface adsorbate molecules are within the plasmonic field or "hot spots." We believe this is the fundamental mechanism giving rise to our recently observed intense Raman scattering from a benzenethiol self-assembled monolayer (SAM) coating. A heuristic argument similar to that in the discovery of SERS is that the increase of surface area (~10-30×) cannot account for the ~4-5 orders of magnitude increase in SERS intensity by comparing solid-core gold nanodisk and NPGN. The porous nature must have modified the nanoplasmonic behavior dramatically.

Another heuristic explanation can be applied to the red-shifted plasmon resonance peak. Colloidal gold nanosphere peaks at ~540 nm and is relatively insensitive to size. Red-shifted plasmonic peak is known to be present in solid-core gold nanodisk (peak ~700 nm) and un-patterned, i.e., continuous, NPG thin film (peak ~650 nm). It appears that the combination of NPGN's shape and the fine porous network has further red-shifted the plasmonic peak into the near-infrared regime, at least to 785 nm employed in our experiments. This further red-shift provides a strong indication of synergistic coupling between external shape of a nanoparticle and its internal nanostructures.

Fifth, the highly plasmonic nature of NPGN suggests that it is a good photothermal agent in the near-infrared, which is critical for deep tissue penetration in biomedical applications. Thus, the embedded molecules can be released by light activation. Sixth, the plasmonic heating on NPGN can become an effective light-gated delivery strategy of the internalized molecules at the cellular, tissue, organ and whole body level.

Although NPGN has so many fascinating properties and potentials, it is not well understood. To the best of our knowledge, we are the first to pattern sub-100 nm thick continuous NPG film into 400-500 nm diameter NPGN.

We have established a NPGN fabrication process. Starting with a continuous Au/Ag alloy film and followed by nanosphere lithography, etching and nitric acid leaching, we have repeatedly fabricated NPGN with consistent size and SERS resulting from a benzenethiol self-assembled monolayer coating throughout the NPGN's external and internal surfaces. In addition to ready-to-use dark-field microscope (DFM), localized surface plasmon resonance (LSPR) imager and a shared scanning electron microscope (SEM) we have developed two critical Raman instruments for NPGN characterization. A high-throughput line-scan Raman mapping system has been employed to characterize dense NPGN units over large area. The second Raman imager enables simultaneous random-access of 50 1-micron$^2$ spots within a 100×100 micron$^2$ sample area and has been employed to perform spatially-agile sampling of many individual NPGN units simultaneously. A novel SERS nanoparticle tracking and monitoring system enables the tracking, monitoring and heating of multiple selective NPGN floating in micro system such as biological cells, a critical milestone. This disclosure deepens our fundamental understanding of this new nanoplasmonic material and to guide future implementation of NPGN for modulation and measurement in biological networks.

BRIEF DESCRIPTION OF THE DRAWINGS

The features, nature, and advantages of the disclosed subject matter will become more apparent from the detailed description set forth below when taken in conjunction with the drawings, wherein:

FIGS. 14(a)-(f) show a comparison of sparse and dense NPGD samples, with bright-field white light images in (a) and (d), SERS maps in (b) and (e), and SERS spectra from five different locations in (c) and (f)

FIG. 18(c) shows a continuous NPG film;

FIG. 18(d) shows NPGN;

FIG. 18(e) shows a SERS map vs. bright-field;

DETAILED DESCRIPTION

Although the present disclosure is described with reference to specific embodiments, one skilled in the art could apply the principles discussed herein to other areas and/or embodiments without undue experimentation.

Reference will now be made in detail to certain embodiments of the disclosure, examples of which are illustrated in the accompanying drawings.

Figure 1B:
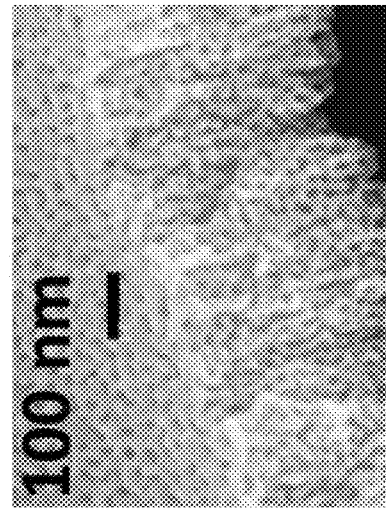
FIG. 1(b) shows 300 nm thick NPG thin film.
Figure 1D:
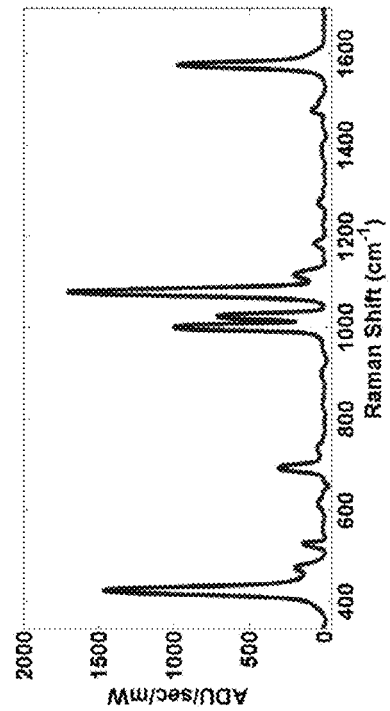
FIG. 1(d) shows benzenethiol SERS from NPGD with SERS EF ~$10^{8-9}$.
Figure 1A:
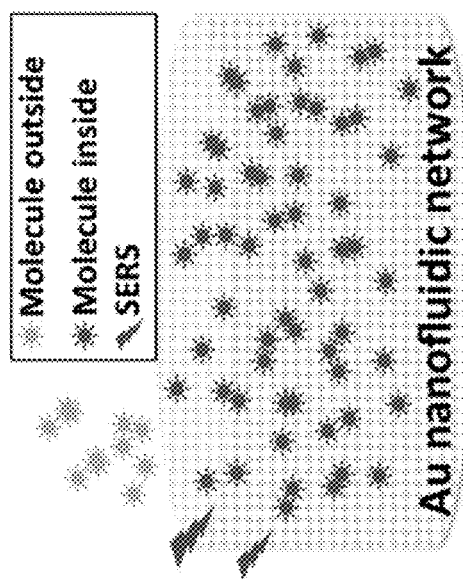
FIG. 1(a) shows an Au nanofluidic architecture.
Figure 1C:
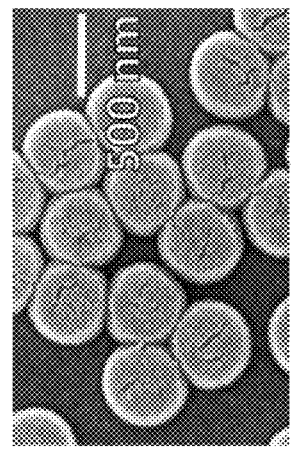
FIG. 1(c) shows patterned NPGD with diameter 500 nm and thickness 75 nm.

The monolithic plasmonic nanofluidics of this disclosure features an ultra-fine network of Au nanofluidics with channel width ~5-15 nm. The molecular analyte can be plasmonically trapped, its SERS measured, and then released. In this implementation, we exploit the fascinating properties of unpatterned and patterned nanoporous gold as the 3-dimensional sensing volume. As shown in FIG. 1(b), 300 nm thick NPG thin films can be fabricated by free corrosion of Ag from Au/Ag alloy thin films, forming tunable nanoporous structures throughout the film. Depending on the pore size and density, the effective surface area can be increased by ~5-80 fold compared to a flat gold surface. NPG is known to be plasmonic with a broad resonance peak near 600 nm. Thus, we and others have obtained SERS enhancement factor (EF) ~106 using 785 nm laser excitation. Beyond continuous NPG thin films, we have pioneered patterning NPG into discrete sub-micron disks using microfabrication techniques. We have observed 2-3 orders of magnitude increase of SERS from NPG disks (NPGD) with diameter ~500 nm and thickness ~75 nm shown in FIG. 1(c), over and above the enhancement factors for unpatterned NPG. A benzenethiol self-assembled monolayer was employed as the marker and its SERS is shown in FIG. 1(d) using 785 nm laser excitation. The SERS enhancement factor is estimated to be ~10$^{8-9}$ after taking the increased surface area into account. Due to the high porosity, NPG/NPGD at this thickness is semi-transparent, enabling excitation laser light to penetrate through. In addition, NPGD is designed to be about the same size as a highly focused laser spot (full width half maximum ~500 nm); therefore, all the benzenethiol molecules assembled on the disk's surface and in the nanoporous network throughout its volume contribute to the observed SERS.

There are three basic approaches in SERS: colloidal nanoparticles of various shapes, probe-based nanotips, and nanostructured substrates. The colloids are usually made by solution processes, the tips of metallized atomic force microscope (AFM) tips, and the nanostructured substrate by lithographic or self-assembly methods.

Figure 2B:
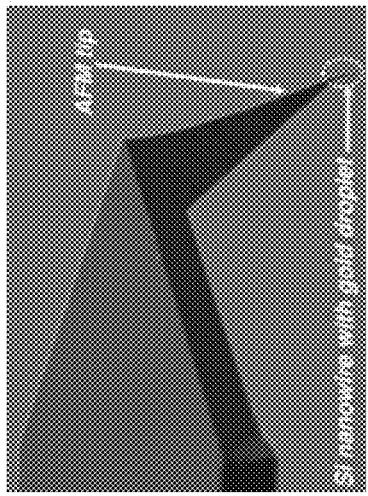
FIGS. 2(a)-(c) show SEM images of Au nanoparticles, a nanotip, and nanostructured SERS substrates.
Figure 2C:
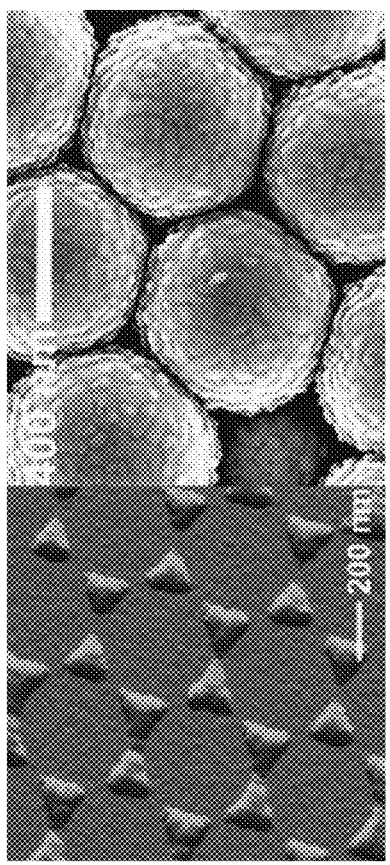
Figure 2A:
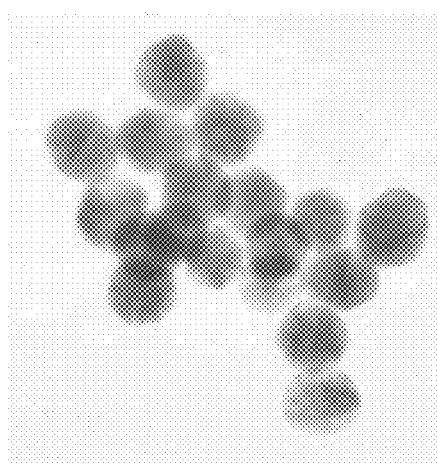
Figure 3B:
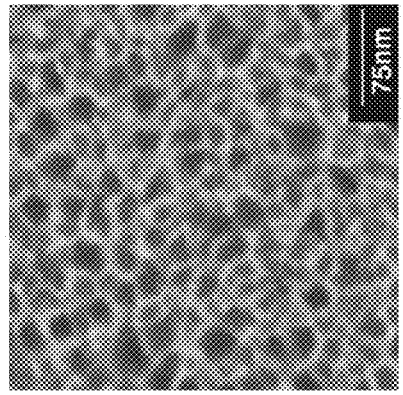
FIGS. 3(a)-(d) show SEM images of Ag nanoparticle decorated anodized alumina, Ag-coated porous silicon, immobilized Au nanoparticle, and a nanorod array.
Figure 3D:
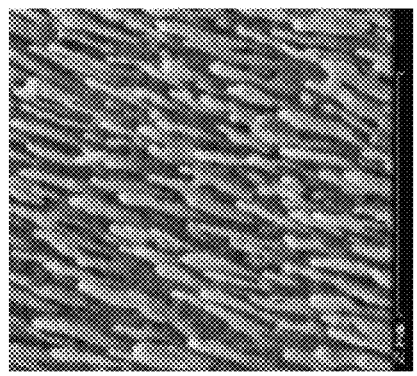
Figure 3A:
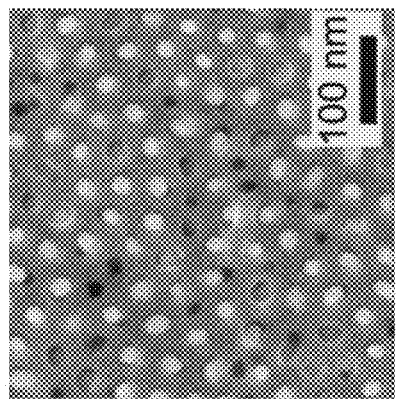
Figure 3C:
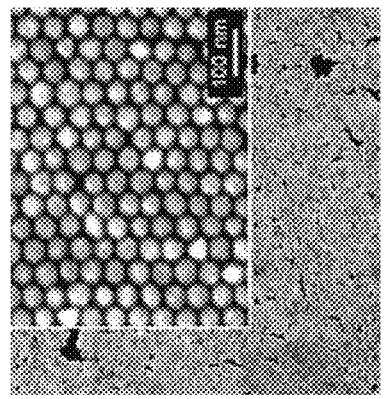

For the colloidal nanoparticle approach (FIG. 2(a)), the nanoparticles usually are functionalized to accumulate at or bind to a specific target through biochemical processes such as antibody-antigen conjugation or coated with thiol or amine terminated reporters or linkers. It is generally difficult to control the aggregation of colloidal NP at concentrations above threshold. Thus, the robustness and repeatability of SERS sensors based on this scheme is relatively low. In particular, it is difficult to quantify the analyte concentrations due to the uncontrollable aggregation.

The nanotip scheme (FIG. 2(b)) is called tip-enhanced Raman spectroscopy (TERS) because the plasmonic enhancement arises from the close "contact" of a tiny gold tip and the sample of interest. TERS, like atomic force microscope, is an excellent imaging tool with nanometer spatial resolution, but it is difficult to incorporate in sensors because only one tiny point is measured at a time. It is challenging to have the target analyte of interest right at the nanotip, particularly at low analyte concentration.

The nanostructured substrate scheme, on the other hand, can potentially provide better repeatability and robustness for sensor applications because of its well-defined nanostructures. However, the enhancement only occurs right on top of the nanostructured surface. In other words, for molecules to be plasmonically enhanced, they cannot be more than a few nanometers farther away from the substrate. Therefore, most state-of-the-art SERS sensors rely on chemically or biochemically functionalized surfaces to improve the analyte-nanostructure affinity, as well as to gain selectivity. Nevertheless, reliable and consistent ways to fabricate high-density, large-area nanostructured substrate are still an active research pursuit. FIG. 2(c) shows representative SERS substrates developed in Prof. van Duyne's group at Northwestern University. Based on nanosphere lithography (NSL), triangular metal islands (left) can be formed with the polystyrene nanospheres removed. Alternatively, a thicker metal overcoat can cover the polystyrene nanospheres and create a hilly sensing surface (right). SERS enhancement factor ~10$^{6-7}$ has been reported from this type of substrate.

Nanostructured substrates have been made by lithographic methods including electron-beam, optical, nanoimprint, interference, and hybrids. SERS substrates are also made by randomly etched surface or self-assembled nanoparticles such as Ag-decorated anodized alumina, Ag-coated porous silicon, immobilized Au or Ag nanoparticle and nanorod arrays (FIG. 3(a-d)).

We can quantify the 3-dimensional property of a SERS substrate using the effective surface area-to-projected surface area ratio (ESA/PSA). For most planar SERS substrates, this ratio is close to 1. The ratio is between 2 and 10 for substrates that feature more significant surface topography such as the immobilized nanoparticle substrate in FIG. 3(c) with a ratio ~3; the nanorod substrate in FIG. 3(d) with a ratio ~10.

We have been developing novel low-cost SERS substrates over the past 2 years. As an example, FIG. 4(a) shows the scanning electron micrograph (SEM) of a SERS substrate fabricated by physical vapor deposition, during which Au nanoparticles randomly seed on a silicon or glass substrate and form isolated nanoislands.

Figure 4B:
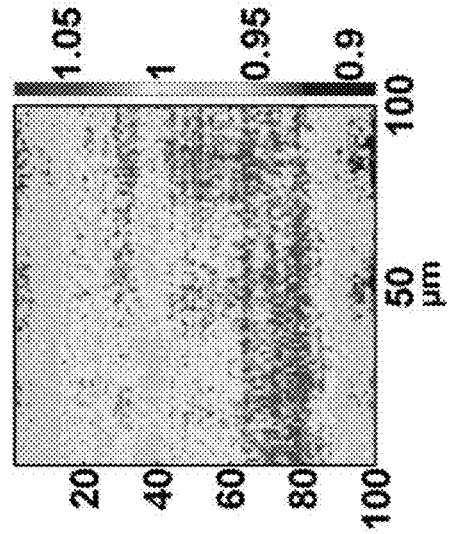
FIG. 4(b) shows a large-area, high-resolution SERS map of benzenethiol self-assembled monolayer (SAM)
Figure 4C:
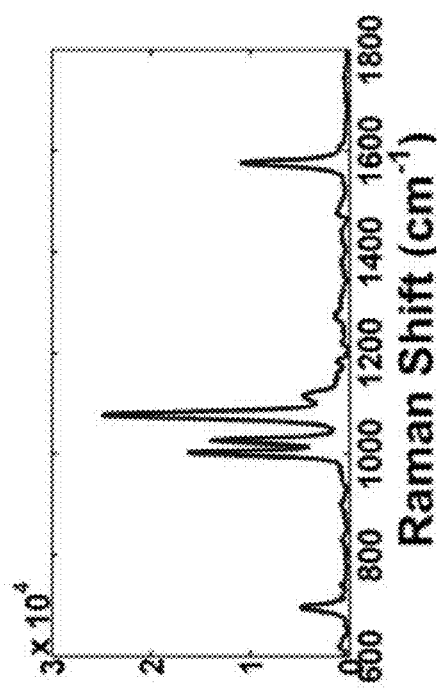
FIG. 4(c) shows a benzenethiol SERS spectrum.
Figure 4A:
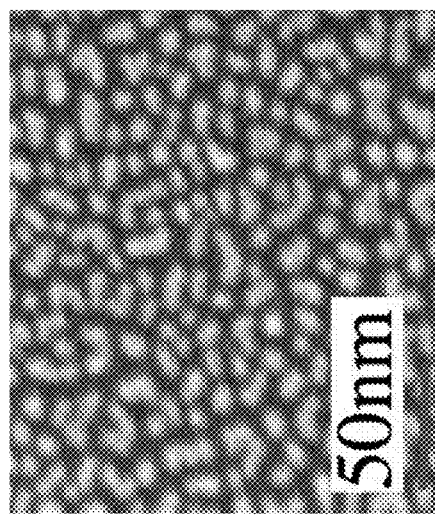
FIG. 4(a) shows a SEM image of sputtered gold nanodots.

High-resolution SERS maps are generated using the 1575 $cm^{-1}$ peak of benzenethiol self-assembled monolayer (SAM) over an area ~100×100 $\mu m^2$ and several sites across each coverslip (FIG. 4(b)). Excellent uniformity (<±5%) has been observed with an enhancement factor ~$10^7$. A high-quality SERS spectrum obtained from ~$10^6$ molecules (<10 atto moles) in 30 sec is shown in FIG. 4(c)).

Figure 5B:
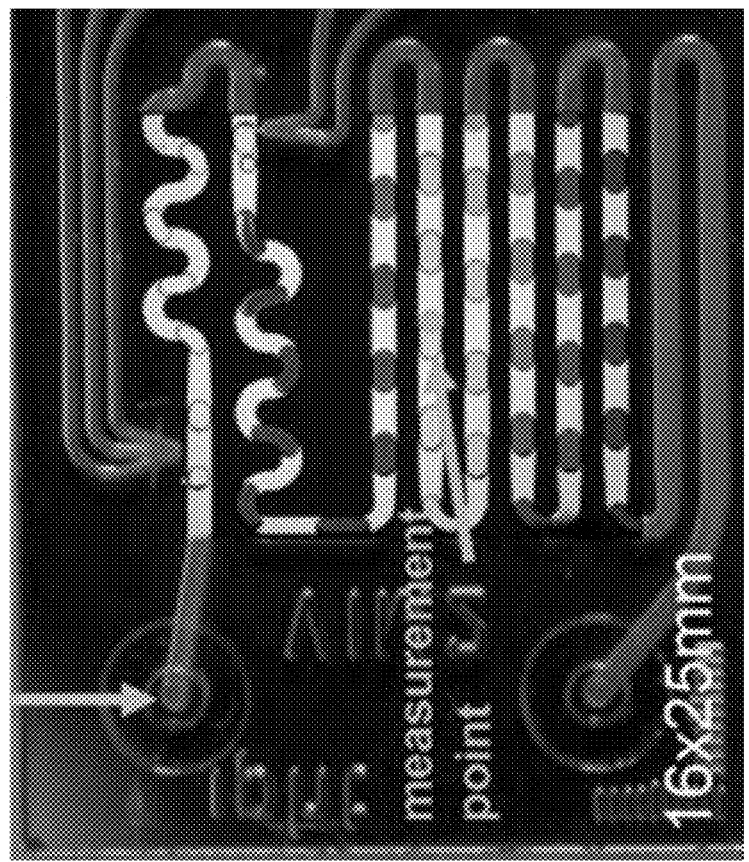
FIGS. 5(a)-(c) show SERS integrated with microfluidics.
Figure 5A:
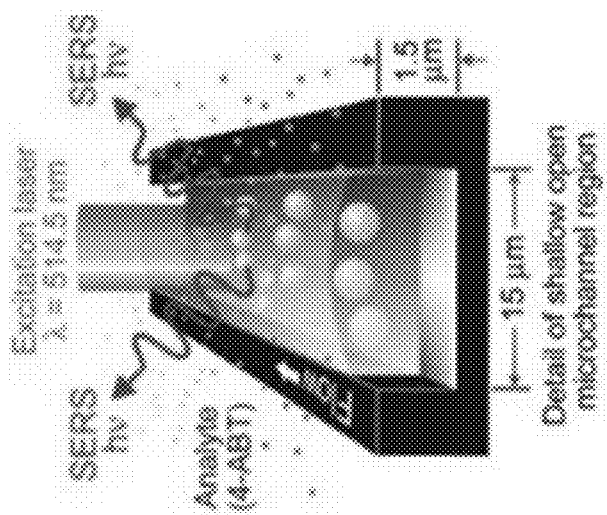
Figure 5C:
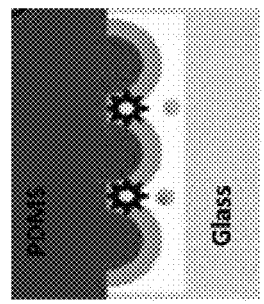
Figure 5D:
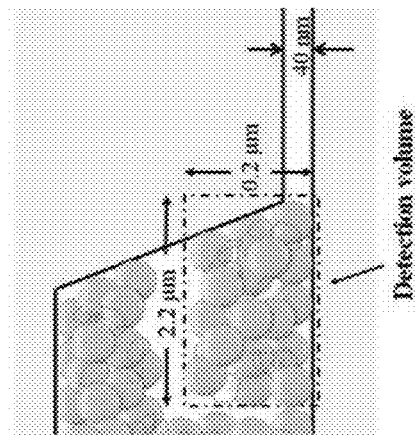
FIGS. 5(d)-(f) show SERS integrated with nanofluidics.
Figure 5E:
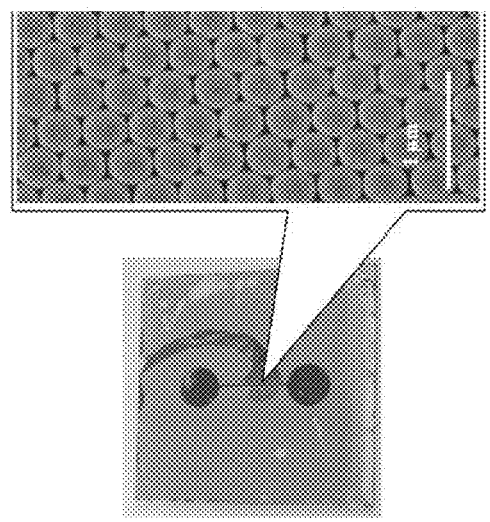
Figure 5F:
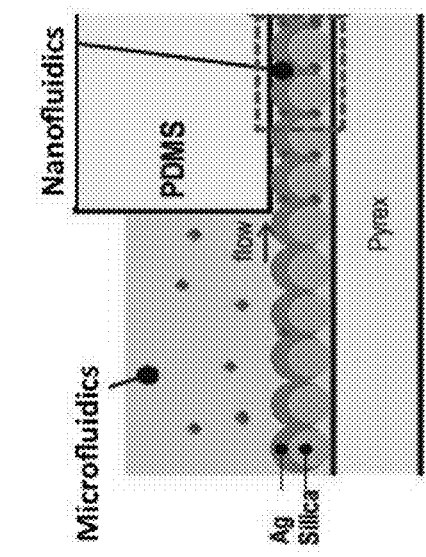

Integration of micro/nanofluidics with SERS-based detection is attractive because SERS could allow label- and surface functionalization-free, multiplexed sensing. In principle, any SERS sensing surface can be fabricated or placed inside a micro/nanofluidic channel to achieve the basic level of integration. There are numerous examples in the literature that utilize micro/nanofluidics mainly as a sample delivery tool. Although the SERS sensor is "integrated" inside micro/nanofluidics as, the potential synergy between the two has not been explored (FIG. 5(a-c)). To improve analyte delivery to the SERS surface, shallow recesses have been fabricated in glass and PDMS polymer to create nanofluidics right on top of the SERS sensing surfaces (FIG. 5(d-e)). Recently, a novel way to integrate nanofluidics with a SERS sensor has been proposed in. In their experiments, 60 nm colloidal gold nanoparticles are first accumulated by geometrical constraints inside a microfluidic channel (FIG. 5(f)). The analytes are then flowed through the gap space between the nanoparticles. They have demonstrated the detection of trace amount of β-amyloid, a potential biomarker for the Alzheimer's disease. As shown in FIG. 5(f), the effective detection volume is ~200 nm in height, thereby suggests a ~3-nanoparticle stack. Thus most of the vertical real estate in the nanofluidic channel is occupied by solid gold. From the above examples, we conclude that an effective way of fabricate plasmonic nanofluidics remain an elusive target.

Although a highly-focused laser spot is capable of trapping microparticles in the far-field, the gradient-based trapping mechanism becomes ineffective when the particles become smaller and enter into the so-called Rayleigh particle range. Although far-field trapping of sub-50 nm Au nanoparticles has been demonstrated, the required laser power is large to overcome the Brownian motion. Plasmonic trapping, on the other hand, can overcome these difficulties due to the ability to localize and enhance light in the near-field. Plasmonic trapping has been demonstrated as a promising technique using thin metal films, metal patches, sharp metal tips, and gap antennas. However, plasmonic trapping of molecules is still a challenge using existing nanostructure configurations. We envision the synergy between nanofluidic confinement and plasmonic trapping can achieve stable molecular trapping.

Recently, nanoporous gold (NPG) has drawn significant attention for its excellent performance in selective oxidation at low temperature. The enhanced low-temperature performance is attributed to the ultra-high surface area (~10-50×) of NPG compared to flat surfaces. Taking advantage of large surface area is not a new idea; however, non-monolithic techniques rely on random decoration of ~5 nm gold nanoparticles on a support substrate and suffer from nanoparticle sintering at elevated temperature, thus degrading the performance and the useful life-time of gold catalyst. In addition, it is challenging to build a truly 3-dimensional nanoporous network using layered assembly of tiny Au nanoparticles. On the contrary, NPG features a continuous porous thin film without the need of a support substrate, thereby increasing long-term stability. In addition to catalysis, the large surface area of NPG has been used in low contact impedance microelectrodes.

Figure 6B:
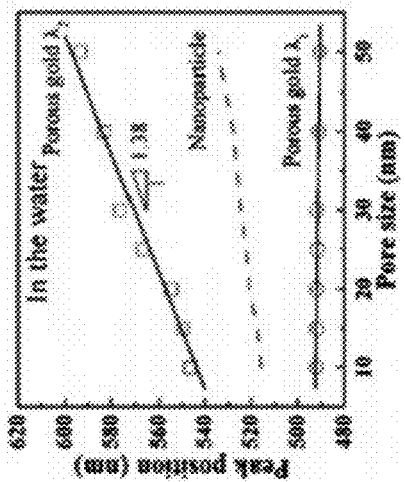
FIG. 6(b) shows LSPR peak position vs. pore size in NPG films.
Figure 6D:
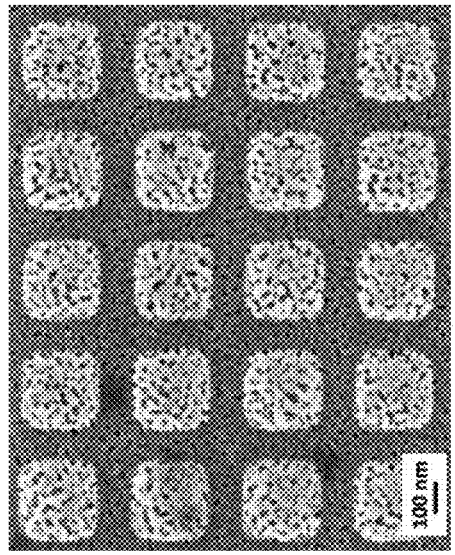
FIG. 6(d) shows mechanically densified NPG film.
Figure 6A:
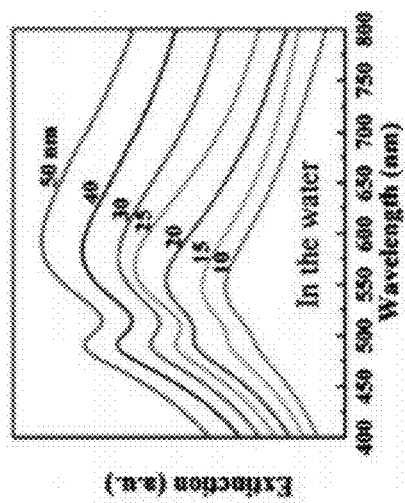
FIG. 6(a) shows LSPR spectrum vs. pore size in NPG films.
Figure 6C:
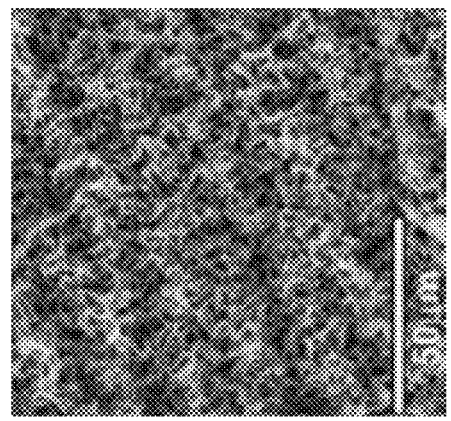
FIG. 6(c) shows SEM of mechanically wrinkled NPG films.

More recently, the plasmonic aspect of NPG has begun to be explored. The plasmon resonance peak determined by absorption spectroscopy has been characterized with respect to pore size and density with results shown in FIG. 6(a-b). As-fabricated NPG and mechanically wrinkled or densified NPG thin films have been demonstrated to be SERS active (FIG. 6(c-d)). From the fabrication standpoint, the starting NPG films in these results have been obtained from repetitive hammering and folding of white gold (Au/Ag mixture) into a "leaf" or thin foils, which can etched in nitric acid and subsequently harvested, laying on top of supporting substrate for characterization or further processing. From the patterning standpoint, the only known existing work that claims to have patterned NPG employs mechanical stamping to compress and densify NPG thin films into alternating submicron domains as shown in FIG. 6(d). This patterning technique does not create isolated sub-micron NPG domain. Rather, the NPG thin film is still in one piece. One order of magnitude increases in the SERS enhancement factor was observed from the patterned NPG. This was attributed primarily to grating coupling as a result of the tile-like pattern.

Plasmonic nanostructures can enhance and spatially localize the electric field in an area much smaller than the diffraction limit. As a consequence, plasmonic nanostructures can generate much larger field gradients than that of far-field trapping at the same illumination intensity. The pervasive plasmonic field inside the NPG or NPGD's internal nanofluidic channels can potentially provide 3-dimensional trapping capability, but exactly how is not well understood. When a molecule enters the nanoporous network (~5-15 nm wide "tunnel"), it is physically confined inside the nanopores and immersed in the plasmonic field. Thus it is quite possible that a trapping effect similar to the gap antennas could occur with even higher trapping efficiency. The trapping of molecular analytes can be monitored by SERS, and is the approach we take to study trapping dynamics under various operating conditions.

The basic principle behind optical trapping is the momentum transfer associated with the scattering of light by a particle. Indeed, light carries momentum, hence when an object scatters light, changing the light propagation direction, momentum conservation requires that the object must undergo an equal and opposite momentum change. This gives rise to a force acting on the object.

Figure 7:
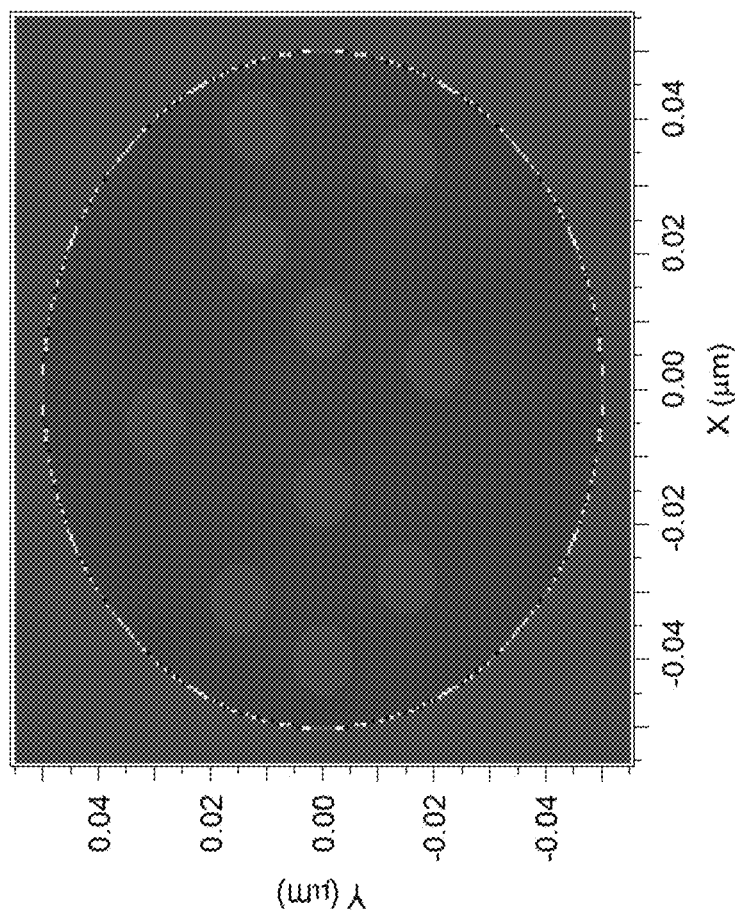
FIG. 7 shows a model for FDTD analysis, including a 3-D model and a refractive index profile of Au disk with ten 10 nm through-holes.
Figure 7:
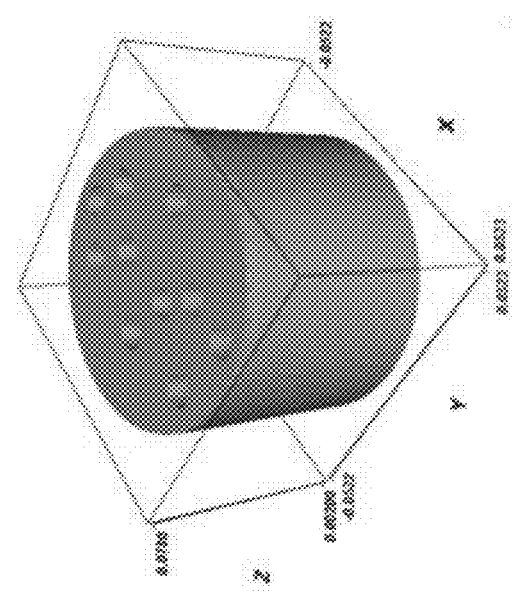

To better understand the plasmonic field distribution, numerical models may be built in, for example, Rsoft and simulated using the finite difference time domain (FDTD) method. In the FDTD framework, the Maxwell's equations are solved iteratively at small time increments. We will compute the electric field distribution inside the nanoporous network and then calculate the gradient force and the scattering and absorption-induced force under plasmon resonance and off-resonance. These forces may be integrated into an equation of motion for local molecules. A preliminary model of Au disk (diameter: 100 nm; thickness: 75 nm) with random through-holes is shown in FIG. 7.

We disclose fabricating NPG and NPGD on silicon substrates. Using either gold or chromium as adhesion layers, the alloy thin film can be deposited to the desired thickness by sputtering of an Au:Ag alloy target using a commercial magnetron source. A magnetic virtual anode is used to prevent electron bombardment of the growing film. To produce NPG thin films, the as-deposited alloy film will be dip etched in nitric acid for a few seconds and then rinsed in deionized water and dried with nitrogen. The porosity may be tuned by using different Au:Ag ratios, optimized nitric acid concentrations and etching time.

To fabricate NPGD, spin coating of polystyrene (PS) beads may be used to form a uniform monolayer, similar to the procedure in nanosphere lithography (NSL). NPGD diameter can be controlled by selecting PS beads of different sizes. The PS bead monolayer can be eroded in oxygen plasma to produce the desire spacing and for additional NPGD diameter and spacing control. The sample may then be sputter etched to produce isolated NPGD. The PS beads will then be removed by solvent and sonication. A detailed fabrication process flow is shown in FIG. 8(a-c).

After fabricating the NPG or NPGD plasmonic nanofluidics, it may be integrated within a microfluidic enclosure for facile sample delivery and experimentation. As shown in FIG. 8(d), standard soft lithography method may be employed to fabricate a microfluidic enclosure using polydimethylsiloxane (PDMS). The height of the PDMS "rooftop" may be ~1-5 µm depending on the photoresist thickness used in the soft lithography process. The exact height is not critical because we are not relying on the PDMS enclosure to create nanofluidics, but to improve the efficiency of sample delivery to the sensor surface.

We may use a home-made microscope to map the LSPR extinction spectra on NPG and NPGD of various pore size, pore density, thickness and diameter. A home-built line-scan confocal Raman microscope may be used to simultaneously acquire SERS image from an area of 130 µm2 with 700 nm spatial resolution, enough to resolve individual NPGDs. To assess SERS activities, we may use benzenethiol which forms self-assembled monolayer on gold surface via the Au—S bond. Following published protocols, we may incubate the sample in 5 mM benzenethiol dissolved in ethanol for 30 minutes, followed by a pure ethanol rinse for 1 minute and nitrogen dry.

We may test benzenethiol in flow-through experiments, comparing samples with continuous laser illumination to those only illuminated intermittently during SERS acquisitions. Non-thiolated dye molecules such as Rhodamine 6G may then be used as the SERS marker. Time-lapse flow-through experiments may be performed with variable laser intensity to study plasmonic trapping. In these experiments, we expect to see the SERS intensity increases faster in samples with continuous laser illumination, compared to those where the laser is on only to acquire the SERS spectrum. The effectiveness of plasmonic trapping will thus be assessed. We may optimize the trapping efficiency by experimenting with NPG/NPGD design and laser power.

We may then study whether the molecular analytes can be released from the plasmonic nanofluidics by reducing the laser illumination duty cycle and increasing the flow rate. A gradual decrease in SERS would suggest the analytes are released from the plasmonic nanofluidics.

Finally, we may study the effect of combined effect of plasmonic trapping and nanofluidic confinement with different analytes by using molecules with different size and configurations under variable laser illumination duty cycle and flow rate. Next, multiple analytes may be simultaneously injected and test whether multiplexed trapping, sensing and release can be achieved.

We have rapidly progressed toward the proposed goals. We have started the FDTD model and simulation. A repeatable NPG fabrication process has been established. Using drop-coating of PS beads, we have obtained NPGD with consistent SERS. Larger-area SERS maps have been obtained from different samples using the home-built confocal Raman microscope.

Figure 9B:
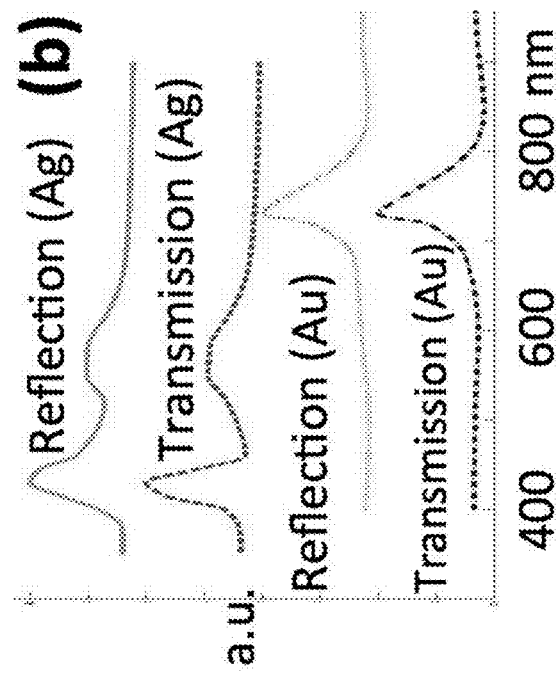
FIG. 9(b) shows a plasmon resonance peak for Au and Ag disks.
Figure 9A:
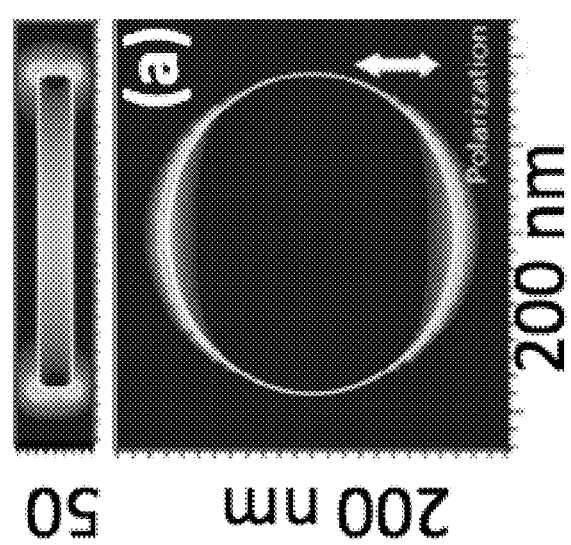
FIG. 9(a) shows E-field distribution near a solid Au disk.
Figure 10:
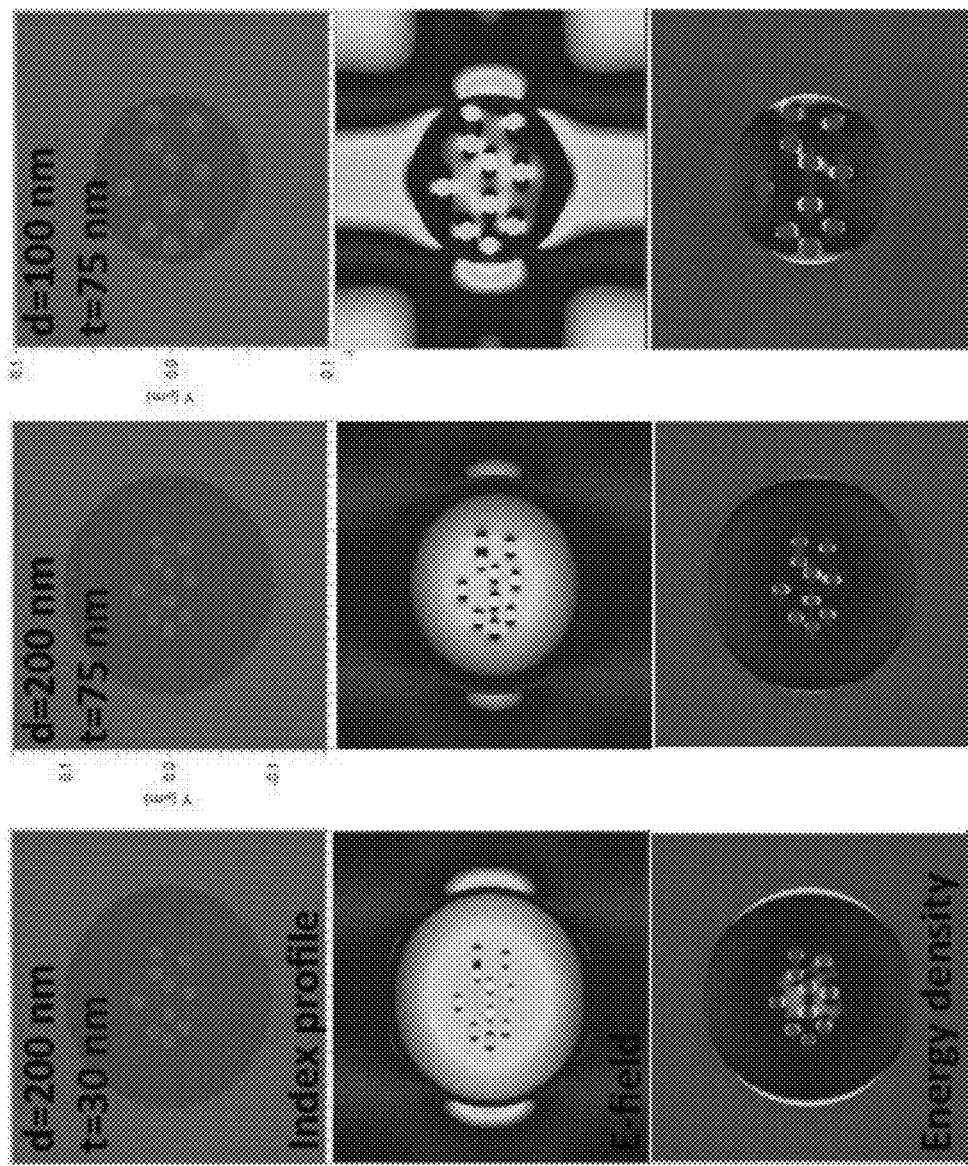
FIG. 10 shows FDTD results from three Au disks with ten 10-nm through-holes.

Solid gold disks with similar external geometry and size are known to be plasmonic at NIR wavelengths. This is confirmed by our simulations as shown in FIG. 9(a-b). Finite difference time domain (FDTD) was employed to calculate the electric field distribution near an Au (or Ag) disk with diameter ~180 nm and thickness ~20 nm. Wavelength-scanned results show that the plasmon resonance peak for Au and Ag are at 720 nm and 410 nm, respectively. As a first step toward simulating NPGD, we simulated a model with random through-holes in Au disks of different sizes (diameter: 100-200 nm; thickness: 30-75 nm; ten through-holes: 10 nm). Results shown in FIG. 10 suggest that there is indeed strong plasmonic field inside these nanoholes. We will further refine the model to incorporate random nanoporosity.

Figure 11B:
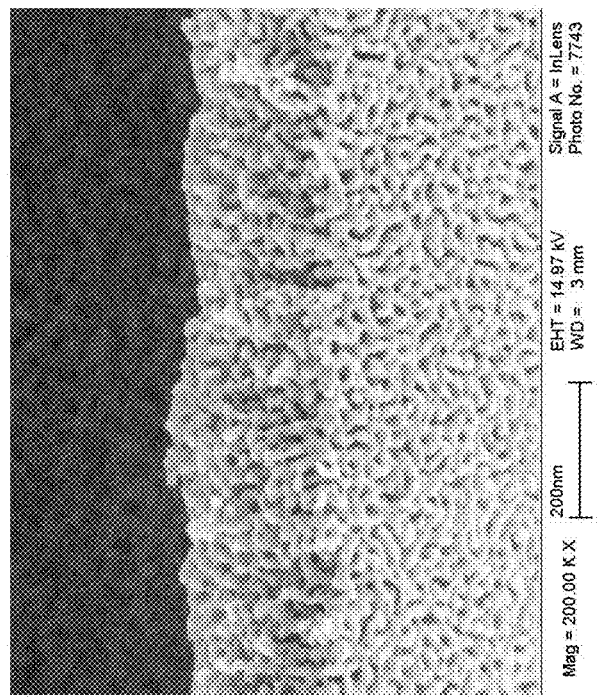
FIG. 11(b) shows a SEM image of a NPG thin films lift off from the substrate to reveal cross-section.
Figure 11A:
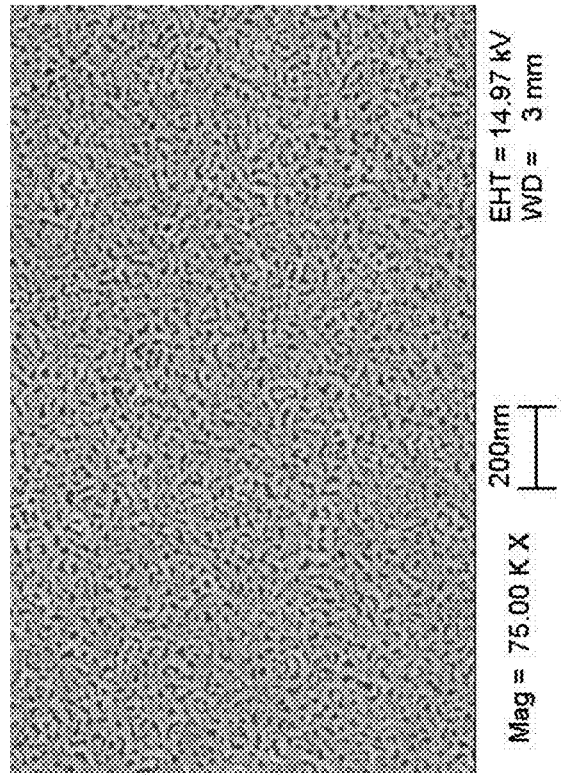
FIG. 11(a) shows a SEM image of monolithic NPG thin films on a silicon substrate

We have fabricated continuous NPG thin films using free corrosion as outlined in this disclosure. FIGS. 11(a-b) show the ultra-fine nanoporous network throughout 300 nm thick NPG films. Pores as small as 5-7 nm are observed.

Figure 12A:
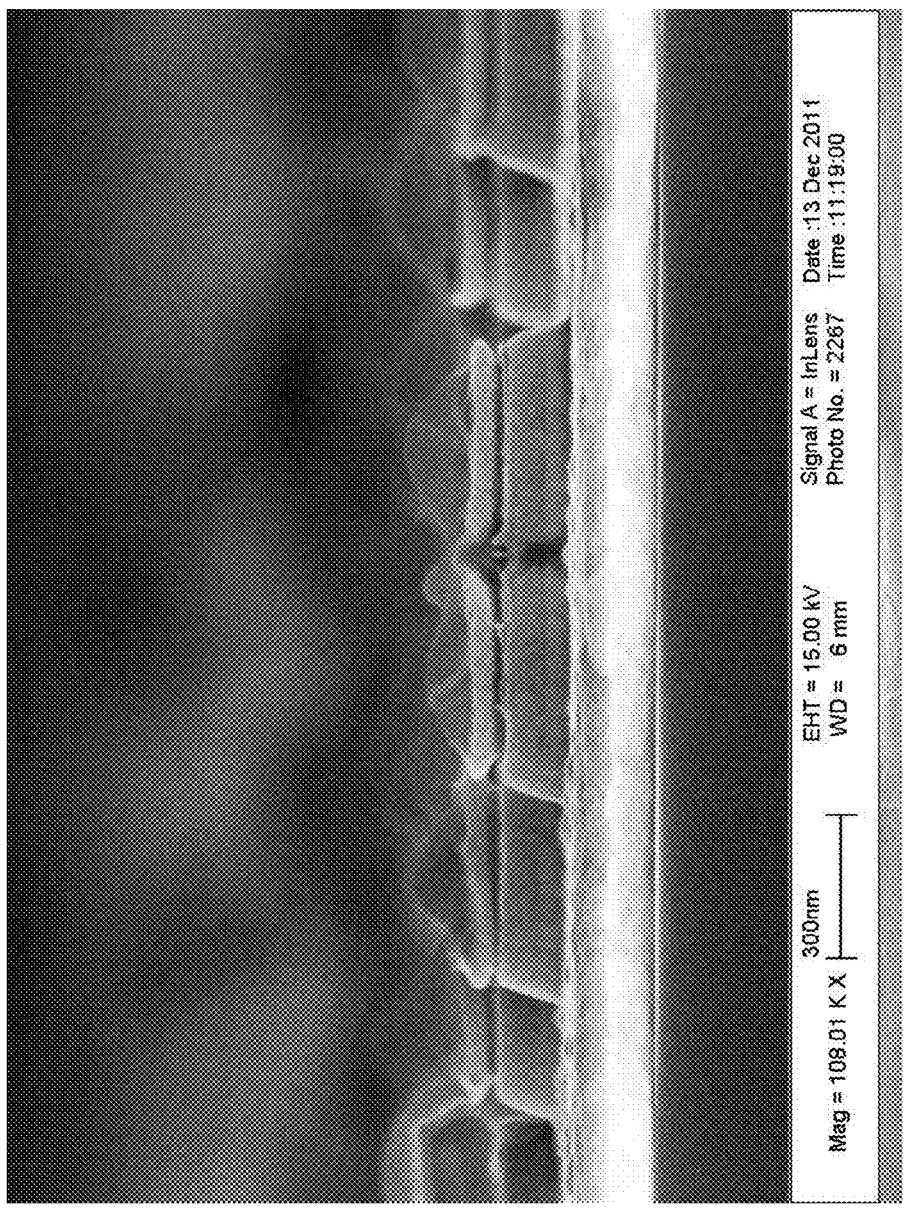
FIG. 12(a) shows a SEM image of patterned NPGD with PS beads on top.
Figure 12B:
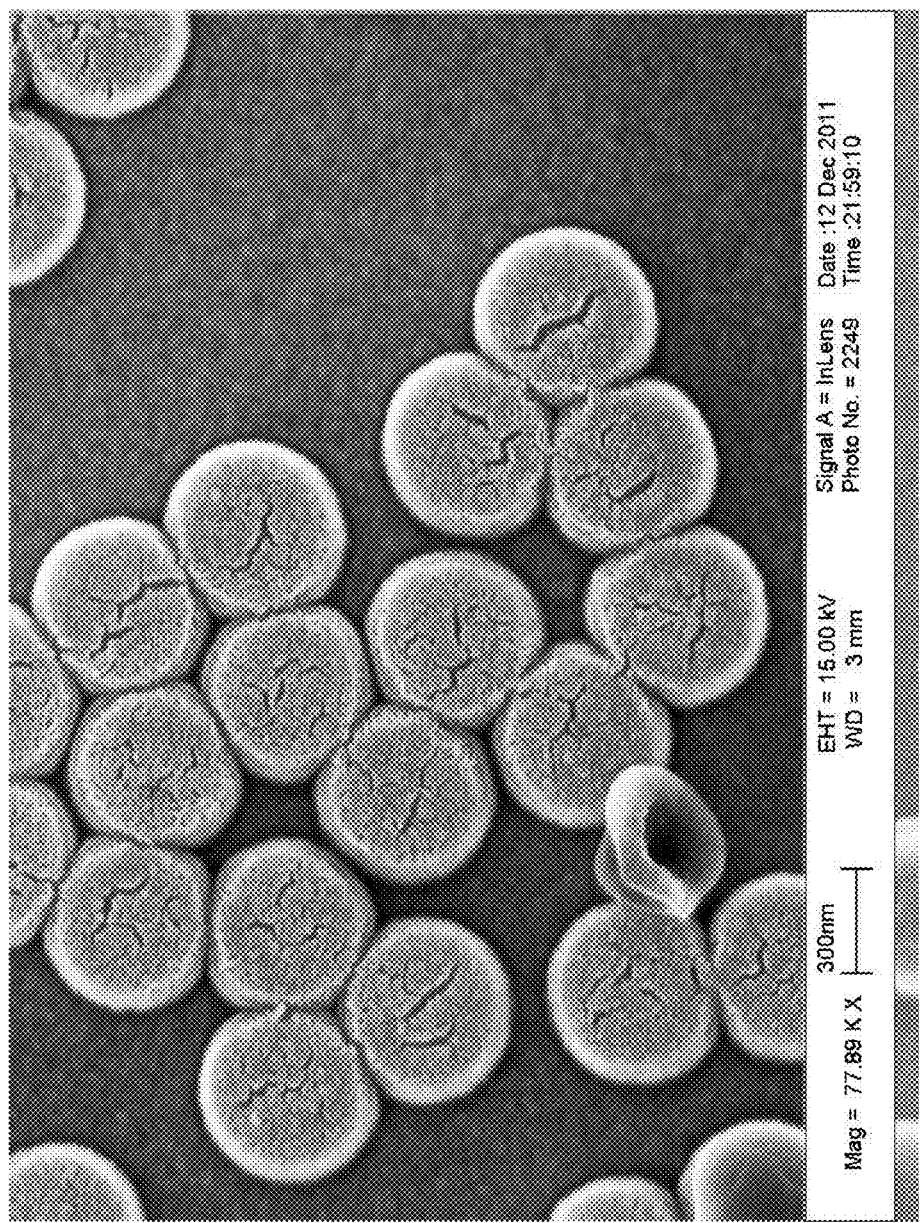
FIG. 12(b) shows a SEM image of patterned NPGD with PS beads removed.

We have fabricated NPGDs using 500 nm PS beads as etch masks, as described in this disclosure. Here the PS beads are drop-coated on the alloy sample as a proof-of-concept demonstration. FIG. 12(a) shows the NPGDs after etching with the PS bead etch mask still in place. FIG. 12(b) shows isolated as well as clustered NPGDs with diameter ~500 nm, proving that the PS beads are effective etch mask.

Figures 13A, 13B:
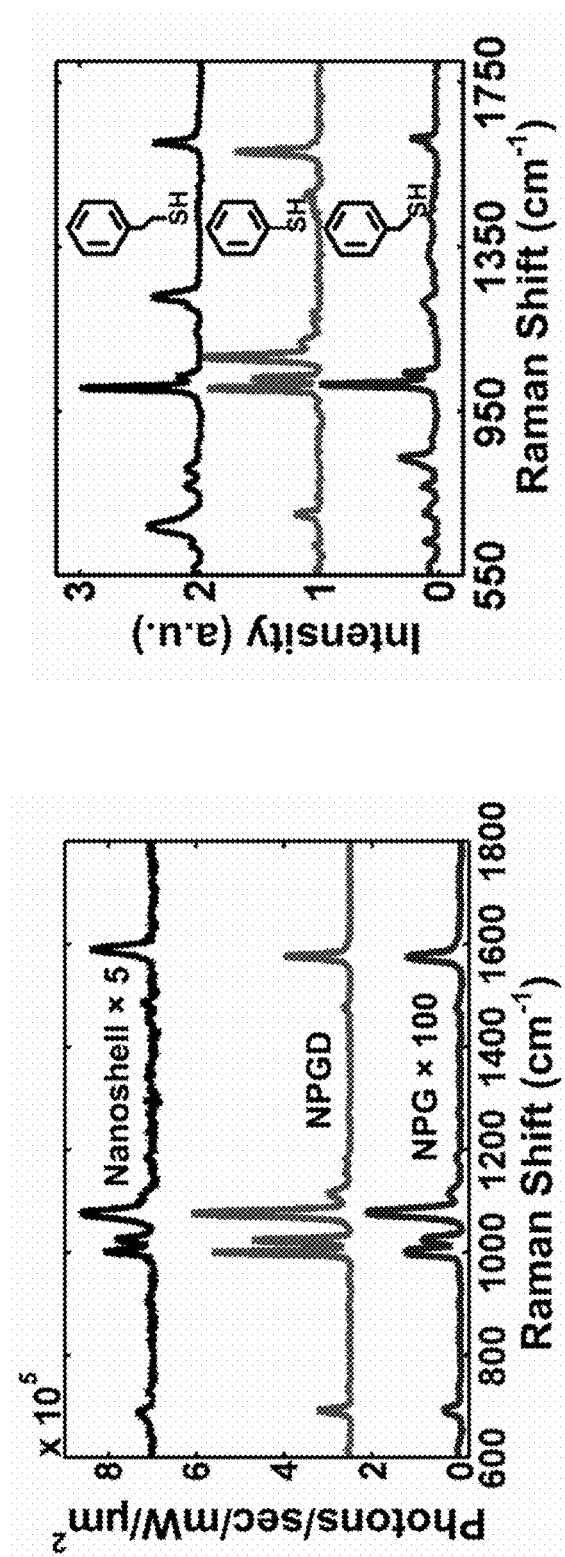
FIG. 13(a) shows normalized benzenethiol SAM SERS from nanoshell, NPGD and NPG.
FIG. 13(b) shows SERS from different thiolated ligands.
Figure 14B:
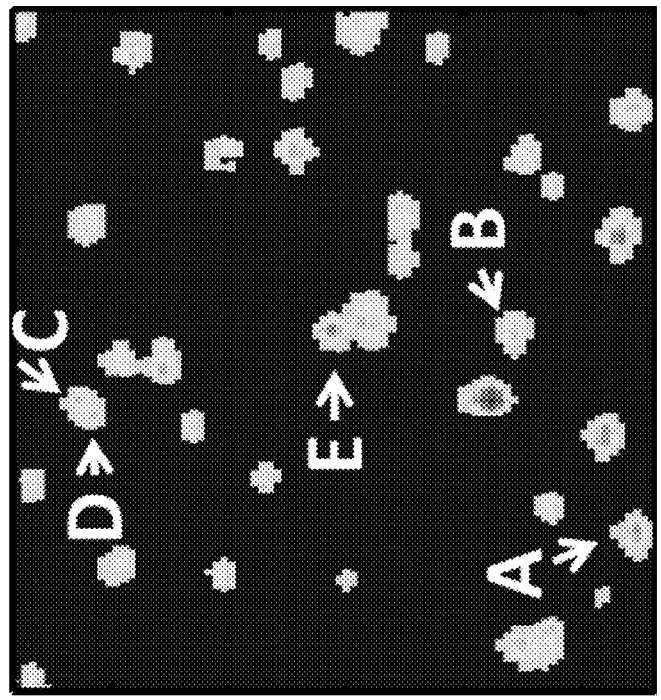
Figure 14A:
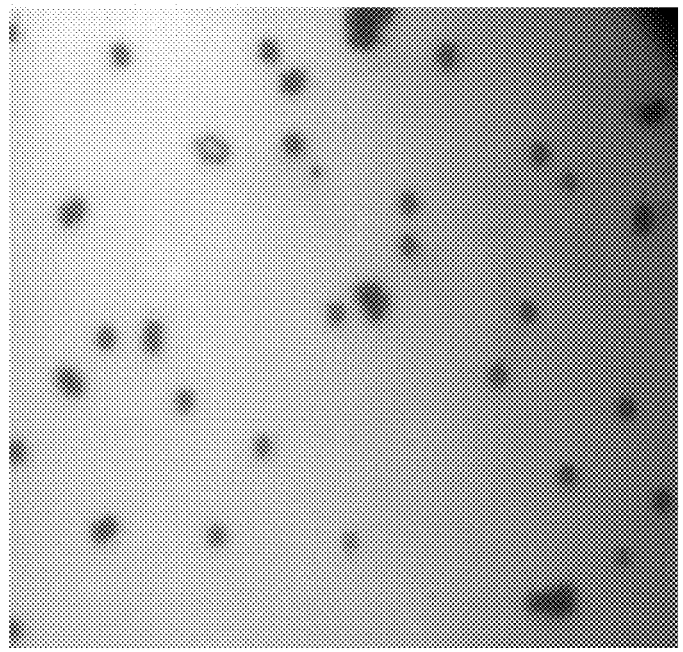
Figure 14F:
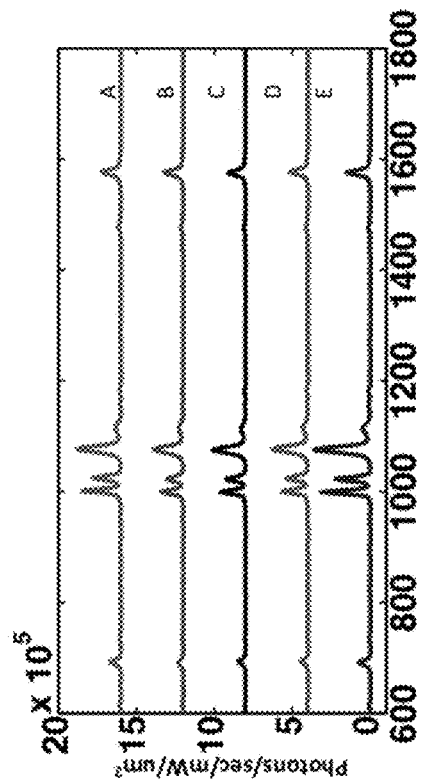
Figure 14E:
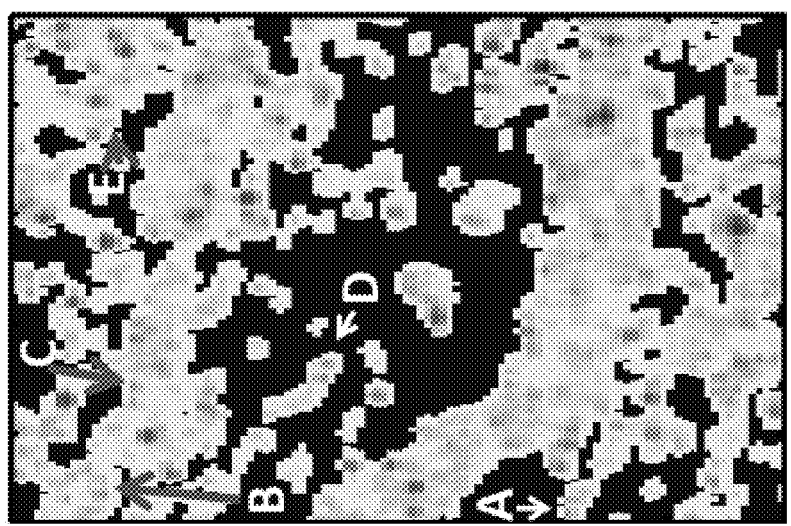

The line-scan confocal Raman microscope has been used to characterize NPG and NPGD over large areas. For the benzenethiol self-assembled monolayer, the normalized CCD count is $3.6 \times 10^5$/(sec-mW-µm$^2$) from NPGD as shown in FIG. 13(a). Since the surface area of this particular NPGD sample is estimated ~10 times larger than its projected area, these photons are contributed by ~68 million molecules (benzenethiol on Au saturation surface density=$6.8 \times 10^{14}$/cm$^2$), or equivalently ~100 atto mole. Based on the signal-to-noise ratio ~400, the current detection limit is ~170 thousand molecules, or equivalently ~300 zepto mole. Comparison of NPGD, NPG and 130 nm Au nanoshells on SiO$_2$ has been made with results shown in FIG. 13(a). The normalized SERS for NPGD is 5× of that from nanoshells and 100× of that from NPG thin films. We have also obtained SERS from other thiolated ligands as shown in FIG. 13(b).

We have mapped different NPGD samples composed of isolated disks as well as densely populated monolayer clusters with results shown in FIG. 14(a) through 14(f). We have obtained perfect image registration between the bright-field white light channel and the Raman channel. The Raman maps are generated using the benzenethiol peak at ~1575 cm$^{-1}$.

When a molecule of interest is near a nanostructured surface of a noble metal such as gold or silver, the localized surface plasmon resonance effect can boost the Raman scattering by many orders of magnitude. Because the LSPR is a near-field phenomenon and decays rapidly with increased separation distance between the molecule and the nanostructure, the SERS signal primarily arises from the molecules residing within a few nanometers of the nanostructured surface. Therefore, it is advantageous for a SERS substrate to have a large surface-to-volume ratio from the standpoint of optical sampling efficiency. Ideally, the detection sensitivity can be enhanced if all the molecules reside in the so-called SERS hot spots, in which plasmonic coupling between adjacent nanostructures introduces further enhancement. However, it is challenging to accurately fabricate high-density SERS hot spots, let alone to accurately place molecules at these hot spots.

NPGD not only provides a high surface-to-volume ratio currently not achievable by other nanostructures or nanoparticles, but also synergizes the external shape and internal nanoporous network for excellent SERS activity at 785 nm laser excitation. The size of the NPGD is designed to be around a tightly focused laser spot (~500 nm) to enable highly efficient SERS collection.

Nanoporous gold thin films have recently captured intense attention for their high surface area. NPG films (~500 microns thick) have been used as an effective catalyst in low temperature oxidation. NPG thin films have been recognized as a plasmonic material and the LSPR exhibits red-shift to ~600 nm depending on the pore size. It has been demonstrated that the SERS enhancement factor increases from $10^6$ to $10^{8-9}$ after wrinkling the underlying substrate of a 100 nm thick NPG film. It has also been demonstrated that the EF changes from ~$10^5$ to $10^7$ after mechanical stamping and densification of a continuous NPG thin film into a 2-dimensional grating. In both cases, the NPG films were harvested after free corrosion and then placed on a substrate for further processing. The observed EF improvement has been attributed to the formation of hot spots and/or grating coupling effects. Instead of mechanical wrinkling or compacting the NPG thin films, we took a different route by patterning NPG thin films into discrete disks with ~500 nm diameters. Based on results in the literature and our own simulations, solid-core gold disks have a red-shifted plasmon resonance in the 700 nm range. Thus, we expected the combined effect of external disk shape and the internal nanoporous network would result in a synergic increase in the SERS enhancement factor.

Figure 8B:
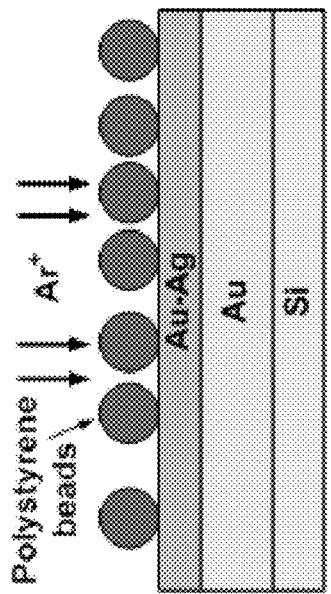
FIGS. 8(a)-(d) show a fabrication process flow for NPG or NPGD plasmonic nanofluidics and a microfluidic enclosure for sample delivery.
Figure 8C:
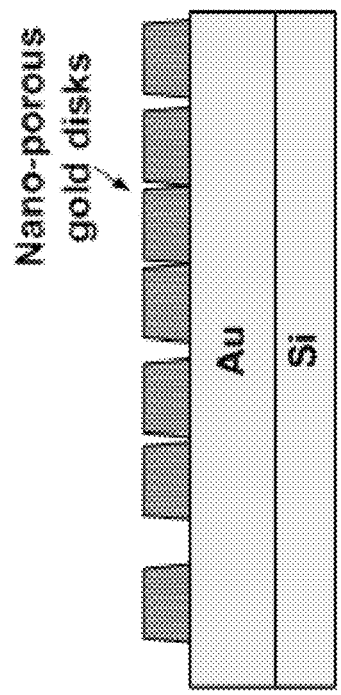
Figure 8A:
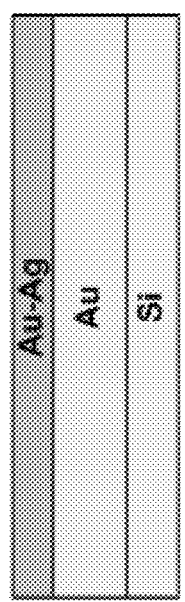
Figure 8D:
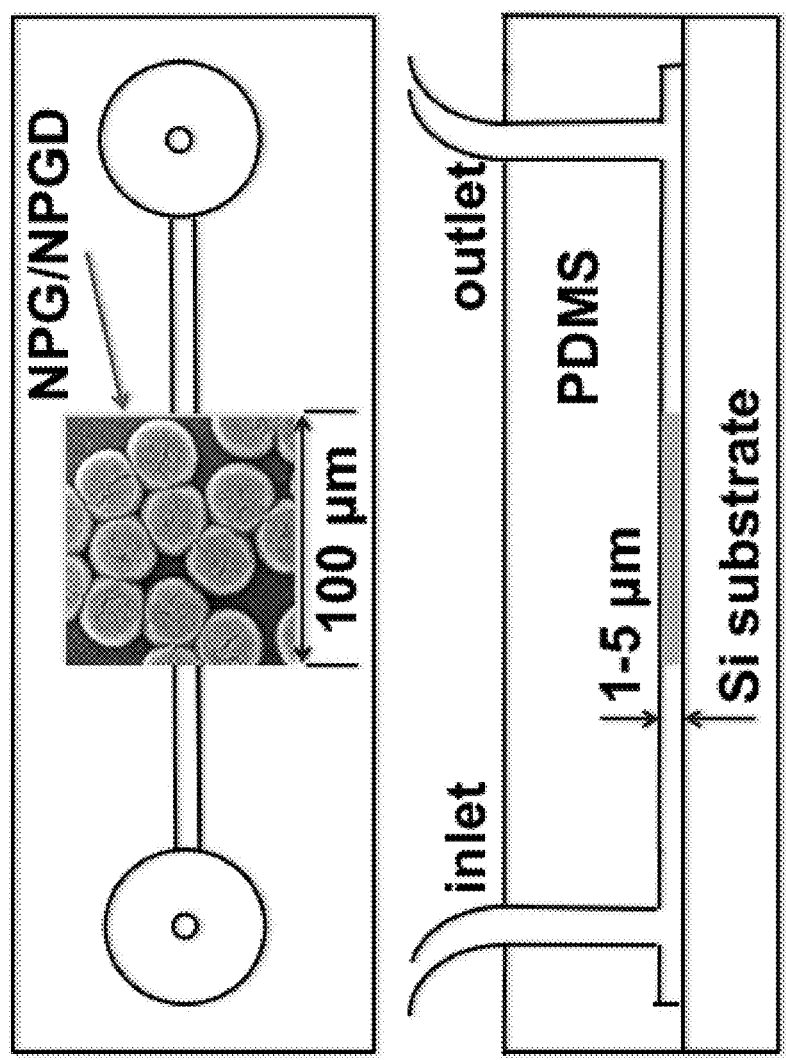

The NPGD fabrication process is shown in FIG. 8(a) through 8(c) and also discussed above. First, a 300 nm thick gold layer is deposited on a silicon wafer followed by a 75 nm Au/Ag alloy film. Next, 500 nm polystyrene beads are drop-coated onto the alloy film, followed by RF-sputter etching using the PS beads as etch mask. The PS spheres are then removed by a combination of solvent and sonication. Finally, free corrosion using 70% nitric acid is employed to leech the silver with 1 sec dip followed by deionized water rinse and nitrogen dry.

The gold and gold/silver alloy films were deposited by DC-magnetron sputtering using a 25 mm magnetron source. The gold film was deposited using 99.99% pure gold target. The composition ratio of the Au/Ag target was 28:72.

The Ar sputtering pressure and power were 5 mTorr and 50 W. A magnetic virtual anode, adapted from the cylindrical magnetron, was used to prevent electron bombardment of the growing film. The deposition rates for the gold and the alloy films were 37.5 nm/min and 25 nm/min, respectively. Sputtering etching was carried out in a homemade reactor with a 150 mm cathode using 99.999% pure argon gas. The power density and argon gas pressure were 0.057 W/cm2 and 2 mTorr. Etch rate of the alloy film was calibrated by scanning electron microscopy to be ~30 nm/min. The etching stops when the entire alloy film not covered by PS spheres is etched away and about ~65 nm of the base gold layer is removed to obtain completely isolated alloy disks sitting on a ~65 nm thick solid gold base. The remaining gold in the etched region is about 235 nm thick.

Figure 15:
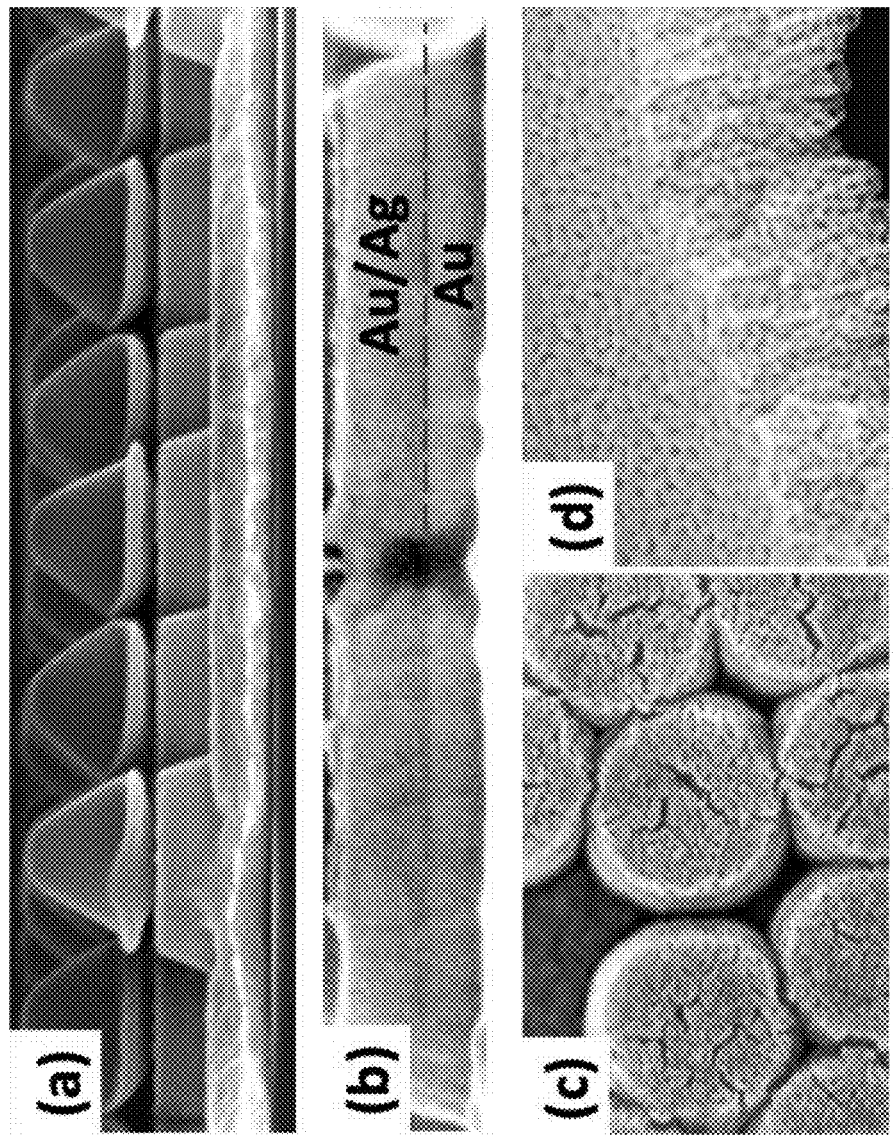
FIG. 15(a) shows etched Au/Ag alloy disks on Au bases.
FIG. 15(b) shows an enlarged image of NPGD sides to show visible boundary between Au/Ag alloy and the Au base.
FIG. 15(c) shows a top view of NPGD.
FIG. 15(d) shows unpatterned NPG thin film.

FIG. 15(a) shows a scanning electron micrograph (SEM) of the PS bead residues covering an etched alloy and gold film stack to confirm the thickness and the effectiveness of PS beads as the etch mask. The boundary between the alloy and gold base is visible in FIG. 15(b). The top surface of NPGD is revealed after the removal of the PS beads and nitric acid corrosion as shown in FIG. 15(c). Here we can observe the ultra-fine nanoporous network similar to that obtained from unpatterned NPG thin films (FIG. 15(d)) fabricated by the same free-corrosion procedure.

Benzenethiol was selected to be the SERS marker for its ability to form a self-assembled monolayer (SAM) on gold via the Au—S bond. Briefly, we incubate the NPGD in 5 mM benzenethiol dissolved in ethanol for 30 minutes, followed by pure ethanol rinse for 1 minute and nitrogen dry. The same procedure was used to coat BT SAM on the unpatterned 75 nm thick continuous NPG thin films and gold nanoshells.

To characterize the SERS activity, we have employed a home-built Raman microscopy system with 785 nm excitation. This system allows us to perform rapid, high-resolution SERS mapping over 100×100 micron$^2$ regions at various places on the substrate. We determine the absolute SERS EF by comparing our SERS spectra to gold nanoshells, which are known to have an EF $10^9$ with 785 nm excitation.

Figure 16:
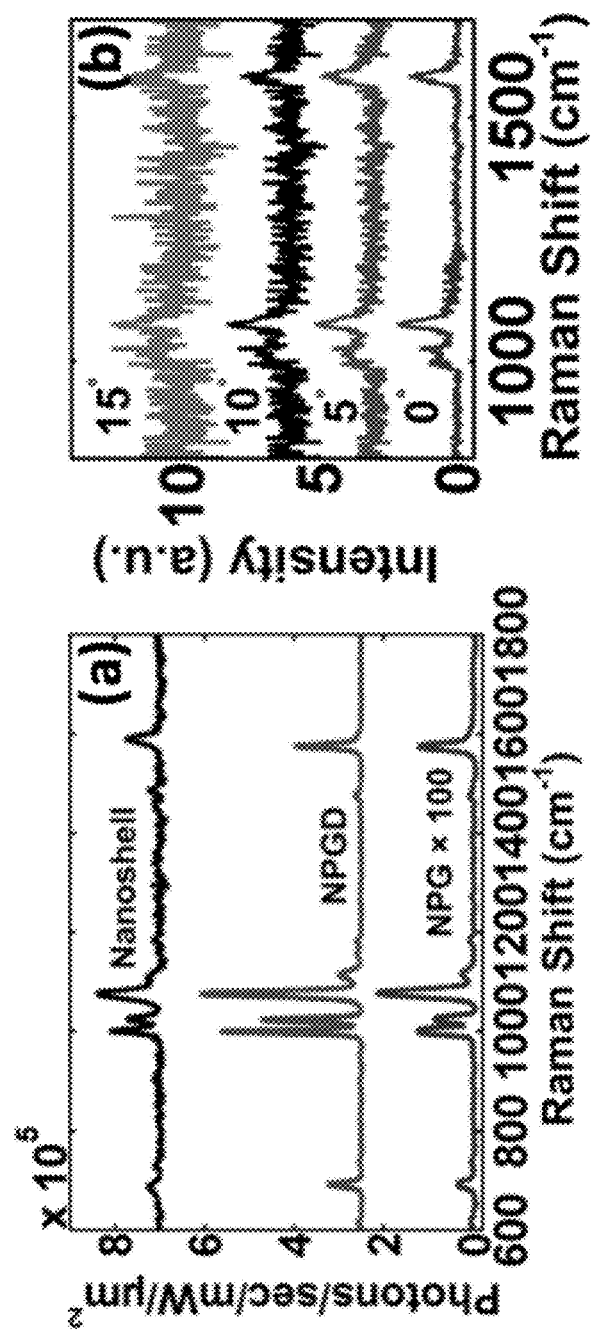
FIG. 16(a) shows normalized SERS from NPGD, unpatterned NPG thin films, and Au@SiO$_2$ nanoshells.
FIG. 16(b) shows SERS from a single NPGD at various detector temperatures.

To establish a baseline for comparison with results in the literature, we compare SERS from unpatterned NPG films, a single nanoshell and a single NPGD with results shown in FIG. 16. Our Raman system has a laser spot size ~1 micron$^2$ matched to the collection optics and a corresponding power density ~0.5 mW/micron$^2$. For the unpatterned NPG, the spectra is effectively collected from a 1 micron$^2$ area; for the single nanoshell ~0.0133 micron$^2$; for the NPGD ~0.196 micron$^2$. From FIG. 16, we observe that the normalized 1575 cm$^{-1}$ peak intensity (counts/mW/sec micron$^2$) of NPGD is ~2.5 times of that from nanoshell, and is ~100 times of that from unpatterned NPG. Since the nanoporous structure and thickness are identical for the NPGD and unpatterned NPG, we can readily conclude that NPGD has an SERS EF ~100 times higher than unpatterned NPG.

Our NPGD have a pore size ~7 nm, porosity ~34%, thickness 75 nm, yielding a total surface area ~10× larger than a flat surface with the same projected area. For nanoshells, the surface area is 4× the projected area. Thus, the surface area ratio of NPGD and nanoshell is ~2.5 given the same projected area. Since the normalized SERS from unit projected area of NPGD is 2.5 times of that from nanoshells, NPGD EF is ~$10^9$, given the EF of nanoshell is $10^9$. Thus, the unpatterned NPG has EF ~$10^7$.

Given that the BT surface density on gold reported in the literature is 6.8×$10^{14}$/cm$^2$, the number of BT molecules on a single NPGD is ~13 million, or 22 attomoles. Since the signal-to-noise ratio for NPGD is ~400 in FIG. 16, the detection limit on average is estimated to be ~32,500 BT molecules (SNR ~1).

Next, we consider the large "capacity" that a NPGD provides. Based on previous estimates, a single NPGD can "pack" 22 attomoles of BT molecules inside a monolithic construct of volume ~14.7 attoL, achieving a molecule-to-volume ratio of ~1.5 mole/L. Comparing to nanoshells with 130 nm diameter, the volume of a single NPGD would be occupied by ~12.8 nanoshells with 4.6 million BT molecules on the surface. Therefore, the NPGD has a molecule-to-volume ratio ~3 times of that for nanoshell aggregates. However, the monolithic NPGD has well defined shape and reproducibility that is challenging to achieve by nanoshell aggregates. As shown in FIG. 16, the BT molecules within a single NPGD (~22 atto moles) can be detected (SNR ~1) by a CCD detector at 15° C. The total laser power was 0.5 mW and the total integration time was 20 sec by summing over twenty 1-sec CCD frames.

We now explore the physical basis of the high enhancement factor in NPGD by comparing unpatterned NPG thin films with patterned NPGD. Since there is no modification to the nanoporous network from our patterning technique, the EF increase is entirely due to the disk formation. A plausible explanation to the substantial EF increase is a red shift of the plasmonic resonance peak toward the laser excitation wavelength (785 nm) by patterning into submicron disk. This is supported by known red-shifted plasmonic resonance peak to ~700 nm for solid gold disks. Next, we compare NPGD to a solid gold disk of similar external dimension which has EF ~$10^6$. Thus, the EF increase cannot be accounted for by the ~10 times increase in surface area. These comparisons suggest plasmonic coupling between the external disk shape and the internal nanoporous network. It is plausible that there are already many potential SERS-active sites at the kinks and corners inside the nanoporous network of the unpatterned NPG thin films, however, are somewhat "dormant". These sites are "activated" after the continuous film is patterned into discrete NPGDs.

Monolithic nanoporous gold disk is a highly effective SERS substrate. The SERS enhancement factor is comparable to gold nanoshells on the per molecule basis, however, about 3 times higher in the molecule-to-volume ratio. The larger capacity could enable more efficient packing of molecules into the 3rd dimension. We note that there has been no attempt to optimize the NPGD for 785 nm excitation, thus, higher EF could be possible at other excitation wavelengths. The optimal excitation wavelength could be tailored for specific applications, e.g., further into the near-infrared region, by various NPGD designs. These aspects will be investigated in future studies. The proposed monolithic NPGD can be fabricated with high reproducibility using the proof-of-concept fabrication process we developed. This process can be easily modified to generate regularly spaced NPGD over larger area. A simple modification is to employ spin coating to form a compact PS beads monolayer as in nanosphere lithography, followed by oxygen plasma erosion of the PS beads to the desired size. We have demonstrated that the detection limit is ~32,500/mW/sec/micron$^2$ BT molecules. We have shown that the BT molecules attached to a single NPGD (~22 atto moles) can be detected using a CCD detector at 15° C. Therefore, NPGD could enable ultra-sensitive SERS sensor using uncooled CCD chips.

Figure 17:
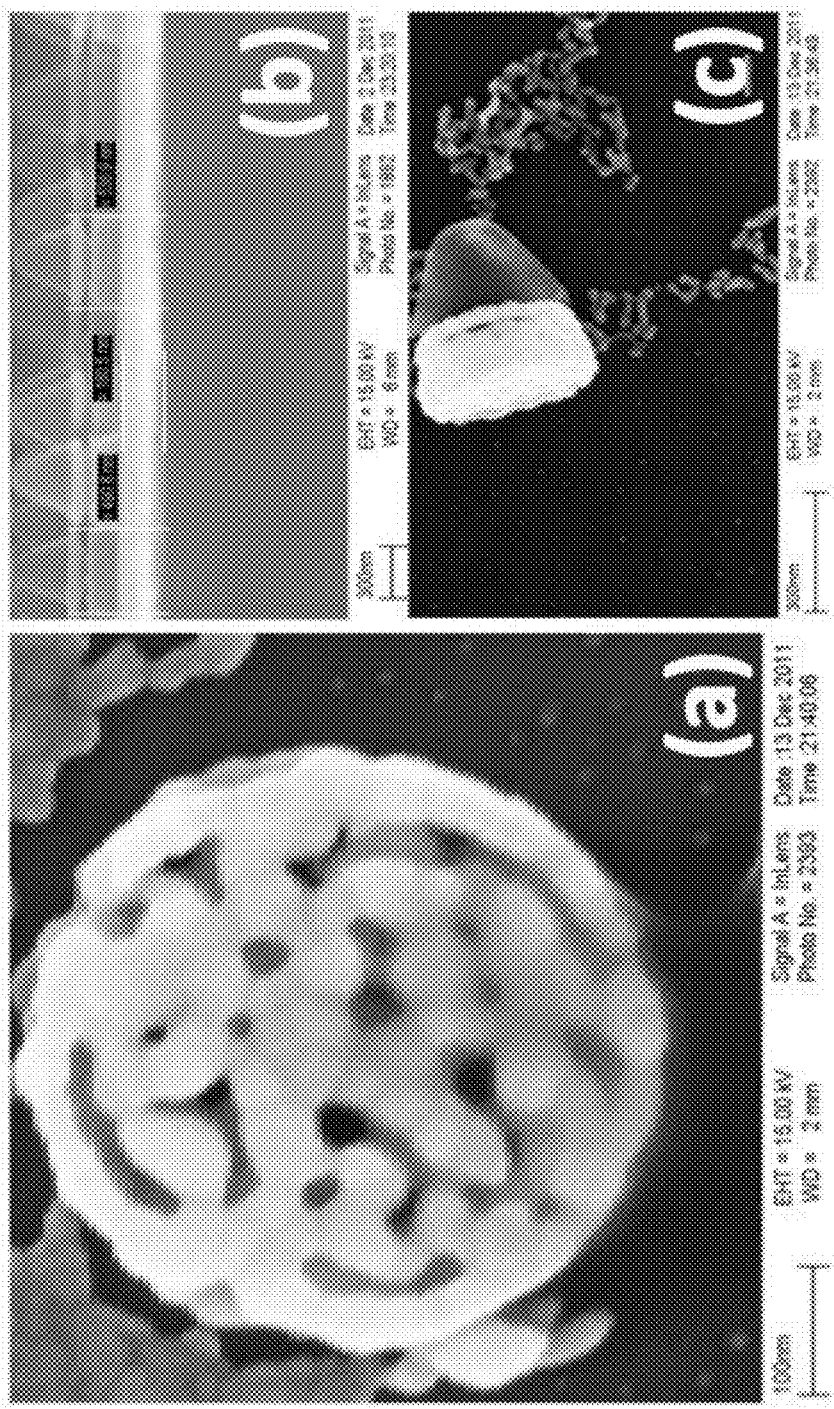
FIG. 17(a) shows a released NPGN.
FIG. 17(b) shows high-density NPGN prior to release with polystyrene beads in place.
FIG. 17(c) shows released NPGN with polystyrene still attached.

Another application of this disclosure relates to medicine. Photodynamic therapy (PDT) is a relatively mature technology where photosensitizers are excited by lasers or diodes to generate highly reactive singlet oxygen, which causes cell death. However, clinical PDT faces several limitations: principally, a lack of molecular targeting specificity, instead relying on the preferential accumulation of the photosensitizer in regions of vascular pathophysiology which only develops in the later stages of a disease such as cancer. Moreover, PDT photosensitizers tend to have limited solubility in blood, poor transport in tissue, and limited biocompatibility. To overcome these barriers, vesicle-based liposomes or nanoparticles similar to those employed in drug delivery have been pursued with some success. It is, however, difficult to monitor the accumulation of these vesicles in the body. Simultaneously optimizing the relevant parameters such as payload volume, solubility, biocompatibility, and stability is still a challenge. In photothermal therapy (PTT), cell death is caused by the hyperthermia condition due to localized heating of nanoparticles by electromagnetic radiation. The first PTT agents were colloidal gold spheres heated by light at the plasmon resonance near 540 nm. Applications were limited however by the strong scattering and absorption of skin, tissue, and hemoglobin at this wavelength. As a result, nanoshells, nanorods and nanocages, where the resonance shifts into the NIR transmission window, were developed for targets up to a few centimeters deep. The tremendous advantage of gold nanoparticles is the ability to coat, or functionalize, them with antibodies that bind only with specific antigens on the surface of target cells. (Such specificity has been challenging for vesicle-based PDT). One goal of this disclosure is to create a synergy between photodynamic and photothermal mechanisms where cell death results from the combined effects of local heating and the toxicity of photogenerated singlet oxygen. The implementation involves our innovation in nanoporous gold nanodisks, one of which is shown in FIG. 17, which could be sealed with a standard self-assembled or a heat-sensitive polymeric overcoat, to carry a photosensitizer to the targeted cells with molecular specificity achieved by the antibody-antigen reaction discussed above for gold nanoparticles. Their accumulation can be easily monitored by surface-enhanced Raman imaging. Once the unbound NPGNs clear the body, NIR illumination will open the seal on the bound particles by plasmonic heating, releasing the photosensitizer payload into the space surrounding the targeted cell. Since the diffusion length of singlet oxygen is very short, less than a few micrometers, the efficiency of generating a high concentration of singlet oxygen exactly where it is needed can be very high compared with the less specific flooding approach of conventional PDT. Moreover, since the NPGN is partially transparent, even the interior exhibits surface plasmon resonance, implying that SERS could be used to monitor photosensitizer release in real-time. This would not be possible with nanosphere, nanoshell or nanocage carriers, since surface enhancement applies only to the molecules within a few nanometers of the gold surface. Once the payload is released, optical power can be increased to heat the surrounding tissue and stimulate the creation of singlet oxygen, whose toxicity would be enhanced at high temperature.

In summary, the synergy may include the following:

1. An increase in efficacy and a reduction in side effects due to an overall reduction in the peak power densities required for the death of targeted cells.

2. A dramatic improvement in the cellular specificity, biocompatibility, and targeted delivery of PDT.

3. Real-time monitoring of nanoparticle density and photosensitizer release in PTT.

Two specific aims of the project are:

1. To design NPGN for optimal plasmonic behavior.

2. Refine two wafer-scale NPGN fabrication methods using atom beam and nanosphere lithography.

3. Characterize the plasmonic heating and singlet oxygen generation of NPGN in solvents, water, and bacterial cell cultures using a combination of SERS, fluorescence and localized-surface-plasmonresonance spectral microscopy.

One NPGN design concept is to pattern nanoporous gold films (~30-100 nm thick) into disks (~60-500 nm in diameter) on a substrate for later harvesting. Nanodisks with such geometry and size are known to be plasmonic in the NIR wavelength, which is confirmed by our simulation. However, there have been no studies on porous nanodisks. We will therefore employ the finite-different-time-domain method to investigate the plasmonic behavior of NPGN with various particle sizes, shapes, pore sizes, and pore density.

The initial film consists of a 27:63=Au:Ag alloy deposited by sputtering a stoichiometric alloy target. We will develop two high-throughput techniques to pattern the Au/Ag alloy film into NPGN using atom beam lithography (ABL) and nanosphere lithography (NSL), both of which are capable of wafer scale fabrication. In ABL, a plasma-deposited negative-tone resist is patterned into nanoislands, 60-500 nm in diameter by neutral helium atom exposure through a stencil mask. The resist pattern is transferred to the Au/Ag alloy by sputter etching. The resist is removed in an oxygen plasma. NPGNs are then formed by leaching the silver in nitric acid. NPGNs are released from silicon substrates during the leaching.

Figure 18B:
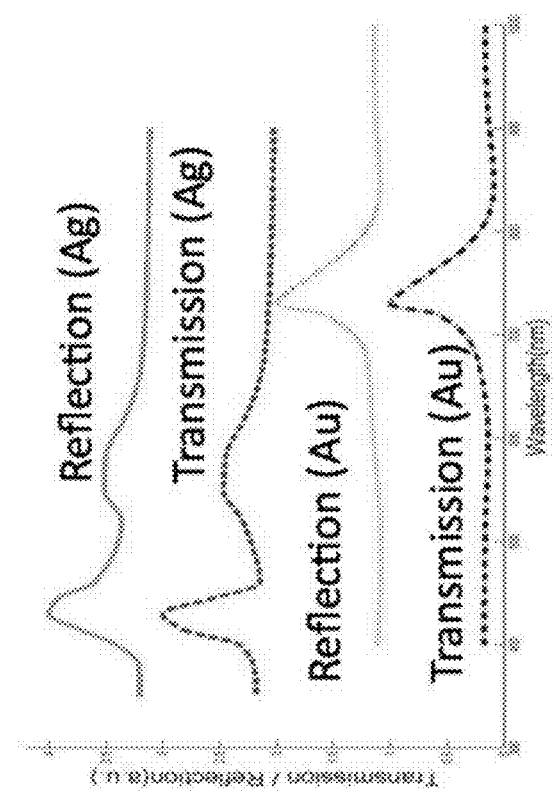
FIG. 18(b) shows extinction spectra for gold and silver.
Figure 18A:
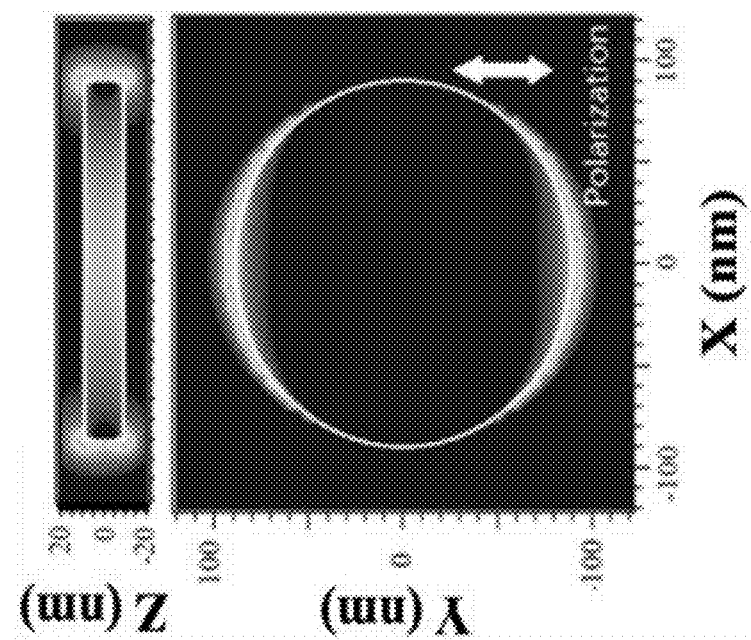
FIG. 18(a) shows an FDTD electric field distribution.

We have studied the plasmonic behavior of non-porous gold and silver nanodisks using the finite-difference-time-domain method. FIG. 18(a) shows the enhanced electrical field at the circumference of a gold nanodisk (d ~180 nm; t ~20 nm). FIG. 18(b) shows the extinction spectra of the nanodisks made of gold or silver. Plasmon resonance is identified at ~420 nm for silver, while ~750 nm for gold. The simulations have been done for solid nanodisks. A red-shifted plasmonic peak to ~650 nm has been observed in continuous nanoporous gold thin film [15]. Therefore, it is our expectation that the proposed NPGN will have more red-shift than either solid gold nanodisk or continuous nanoporous gold film. This is important since it moves the resonance further into the NIR transmission window.

Figure 19:
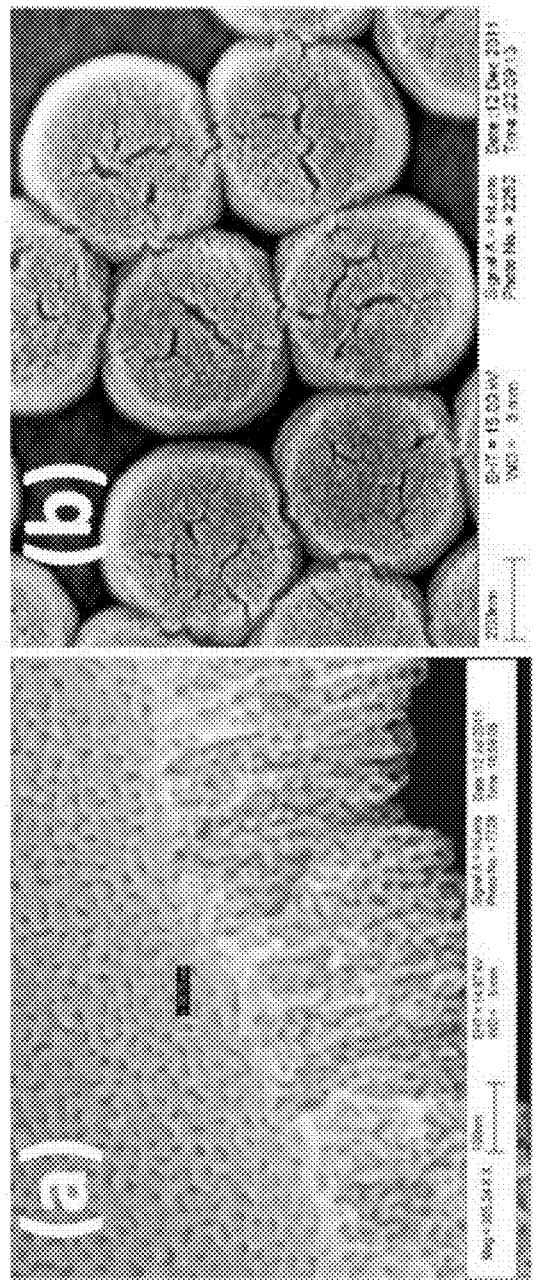
FIG. 19(a) shows a 300 nm thick NPG film.
FIG. 19(b) shows un-released NPGNs.

FIG. 19(a) shows a 300 nm-thick NPG film with highly uniform 5-10 nm pores throughout its volume. FIG. 19(b) shows NPGN islands fabricated by sputter etching using NSL. It is observed that the NPGN's diameter is very close to that of the 500 nm masking polystyrene nanospheres. Cracks are formed in these NPGN due to the good adhesion to the substrate via a continuous Au layer underneath. The cracking issue has been resolved by simultaneous Ag leaching and releasing as shown in FIG. 17. To prove the concept, the polystyrene nanospheres were drop-coated without forming a compact layer. Spin coating and oxygen plasma erosion techniques will be employed in the future to produce compact nanosphere mask for high-throughput fabrication. ABL will be pursued for NPGN with arbitrary shapes.

Figure 20:
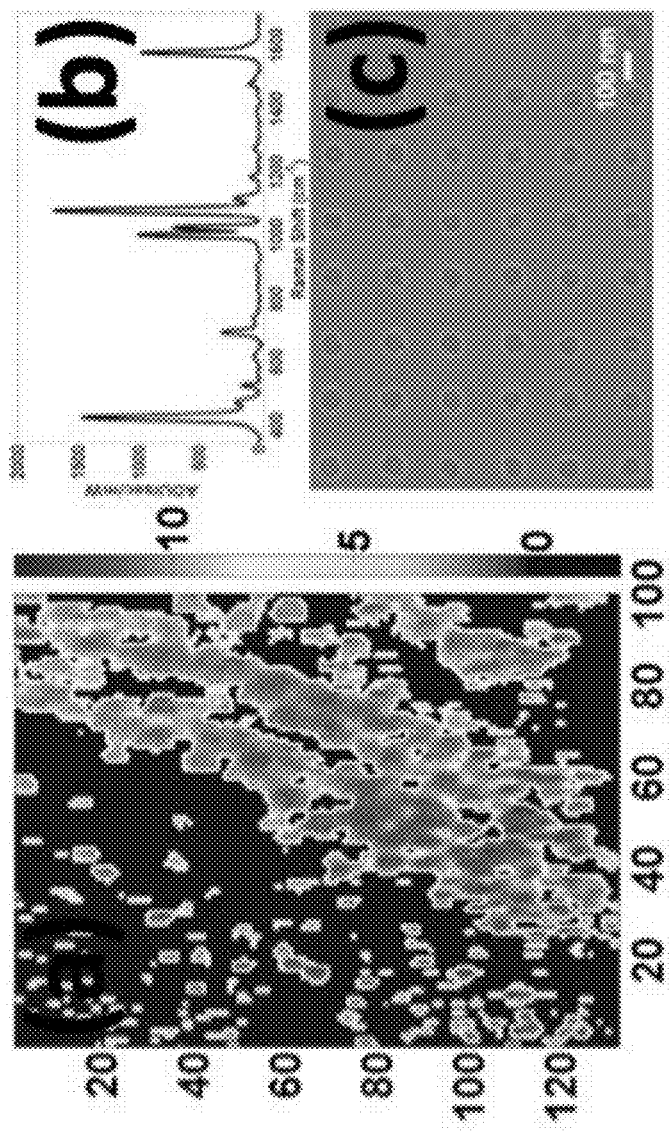
FIG. 20(a) shows a SERS map of un-released NPGN using benzenethiol Raman peak @ 1575 cm$^{-1}$.
FIG. 20(b) shows benzenethiol SERS.
FIG. 20(c) shows ABL patterned photoresist.

We have successfully obtained benzenethiol self-assembled monolayer SERS map from un-released NPGNs (area 133×100 μm$^2$) as shown in FIG. 20(a). The high quality SERS spectrum in FIG. 20(b) (from 1 μm$^2$ area, 0.2 mW/μm$^2$, 1 sec) has signal level ~10$^5$ higher than that from typical non-porous substrates with known enhancement factor 5*10$^5$, as well as published nanoporous Au results, suggesting our NPGN has either ultra-high enhancement factor or volumetric effect or the combination of both. This could be the evidence that benzenethiol SAM coated inside the NPGN's porous network contributes to the SERS signal since NPGN is semi-transparent within the thickness range. This hypothesis may be tested by measuring benzenethiol SERS from NPGN with different thickness. If proven true, we would be able monitor the release of internal adsorbates, i.e., photosensitizers. For the alternative approach using ABL, the requisite resist patterns as shown in FIG. 20(c) have been fabricated.

Figure 21:
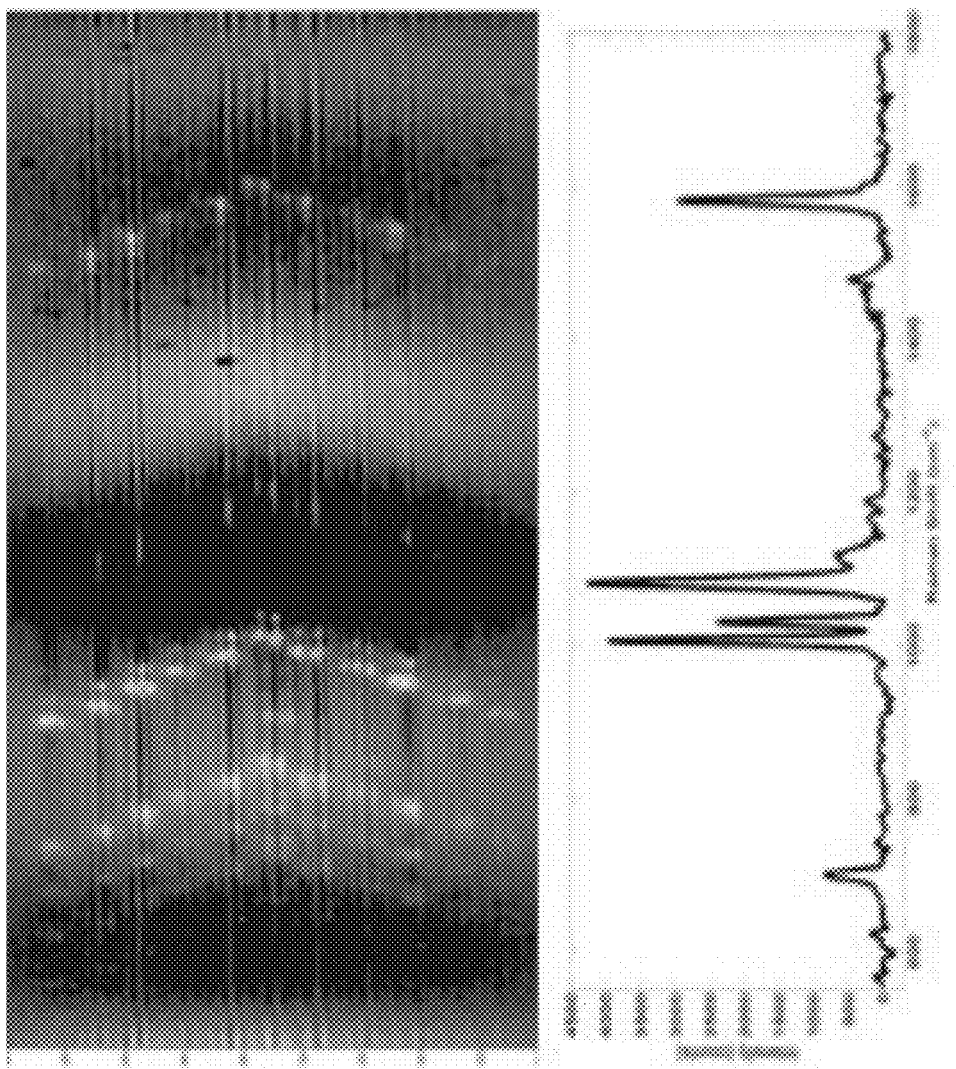
FIG. 21 shows 11-point random access SERS imaging of nanoshells coated with benzenethiol SAM.

A suitable microscope is needed to perform dark/bright field imaging for NPGN tracking, fluorescence and Raman spectroscopy for monitoring various molecules. Starting with a commercial inverted microscope (Olympus IX-71 with dark/bright field and fluorescence capabilities), we have developed a high-throughput Raman microscope based on line-scanning. This instrument can achieve ~100× throughput enhancement compared to a commercial point-scan system. It was employed to generate the map in FIG. 20(a) in 100 sec. Since the NPGN could be moving in the wet or cell culture experiments, we have developed another novel instrument which enables SERS-based particle tracking for ~30 nanoparticles simultaneously. FIG. 21 shows the SERS spectral image from 20 nanoparticles coated with benzenethiol.

NPGN Modeling and Simulation:

Solid gold nanodisks with similar external geometry and size are known to be plasmonic in the NIR wavelength, which is confirmed by our simulation. However, there have been no studies on NPGN. We therefore employ the finite-different-time-domain method to investigate the plasmonic behavior of NPGN with various NPGN sizes, shapes, pore sizes, and pore density.

NPGN Fabrication:

We disclose two high-throughput techniques to pattern the Au/Ag alloy film into NPGN using atom beam lithography and nanosphere lithography, both of which are capable of wafer scale fabrication. In ABL, a plasma-deposited negative-tone resist is patterned into islands, ~30-500 nm in diameter by neutral helium atom exposure through a stencil mask. The resist pattern is transferred to the Au/Ag alloy by sputter etching. The resist is removed in an oxygen plasma. NPGNs are then formed by leaching the silver in nitric acid.

The NSL approach differs from ABL in the formation of a compact monolayer of polystyrene nanospheres by spin coating onto the Au/Ag alloy film. The nanospheres are eroded by oxygen plasma to the desired diameter and then serve as the etching mask, similar to the role of the patterned photoresist in the ABL approach. Although NSL can only pattern round NPGN, ABL permits arbitrary shapes by mask design. The released NPGN may be harvested using a polycarbonate (PCTE) nanofiltration (NF) membrane. The fabrication throughput will be about ~10$^{10-12}$ NPGNs per 4" wafer (wafers can be recycled), adequate for proof-of-concept tests in this pilot project and further pre-clinical tests in cells and small animals.

NPGN Characterization:

SEM, DFM and LSPR microscopy may be performed over a population of NPGN before releasing from the substrate. The NPGN will be coated with benzenethiol SAM as SERS marker. A home-built line-scan confocal Raman microscope will be employed to generate a SERS map over a large area (~100×100 micron$^2$) that covers many isolated NPGN as well as clusters.

Figure 22:
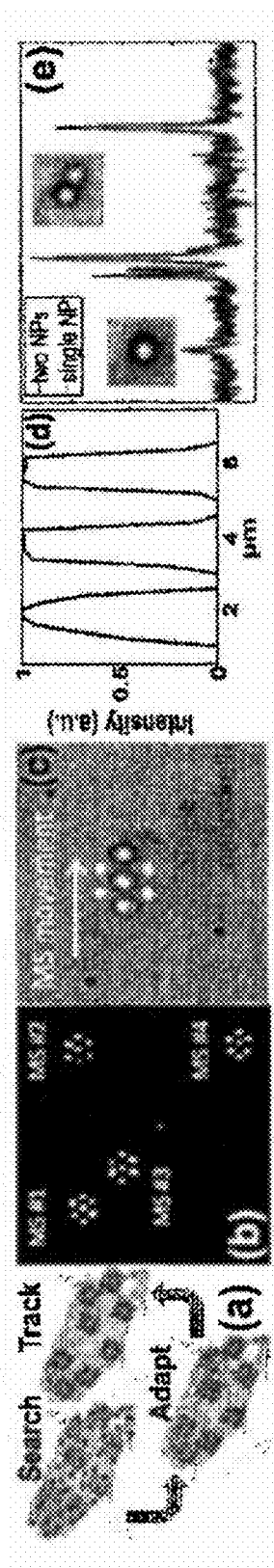
FIGS. 22(a)-(e) show an adaptive SERS based tracking scheme, with motion sensor configuration, tracking experiments, SERS intensity, and single vs. dimer nanoshells benzenethiol SERS.

NPGN Tracking, Monitoring, and Heating:

We disclose a SERS tracking system by splitting a collimated laser beam into many groups of tiny spots using a spatial light modulator (SLM). A CCD camera is used to record SERS from all spots simultaneously. As shown in FIG. 22(a), we start with a random search by flashing random spot patterns over the cell to locate the initial locations of all NPGN (currently we can achieve approximately 50 spots at a time). Then several sub-groups of spots will be allocated, each sub-group for an individual NPGN, to continuously monitor and update as "motion sensors" (MS) as shown in FIG. 22(b) from real data, similar to a 7-element motion sensor. The exact pattern may be optimized. An example MS configuration is shown in FIG. 22(c) and experimentally scanned across a 100 nm nanoshell. FIG. 22(d) shows the 3-channel SERS signals obtained from spots in the center row of this MS, suggesting a tracking accuracy ~1 micron. We can quantify single nanoshell versus dimer purely based on SERS intensity as shown in FIG. 22(d). SERS-based tracking is potentially more sensitive than dark-field microscopy and requires only 1 detector.

We expect to push the temporal resolution down to 1 ms using an electron-multiplied CCD.

The feedback SERS tracking scheme may be implemented using graphic processing unit (GPU) for example in the CUDA (Compute Unified Device Architecture) framework, since it facilitates a C-like development environment with automatic thread management. Using a consumer grade GPU (NVIDIA GeForce GTX 285), Persson has demonstrated 10 ms SLM frame updates for generating multiple holographic optical traps.

Nanoplasmonic Simulation:

FIG. 18(a) shows the electrical field at the circumference of a gold nanodisk (d ~180 nm; t ~20 nm). FIG. 18(b) shows the extinction spectra of the nanodisks made of gold or silver. Plasmon resonance is identified at ~420 nm for silver, and ~750 nm for gold. We may simulate NPGN with various external sizes, pore size and density.

NPGN Fabrication:

FIG. 18(c) shows a 300 nm-thick NPG film with highly uniform 5-10 nm pores throughout its volume. FIG. 18(d) shows NPGN islands after NSL and etching. It is observed that the NPGN's diameter is very close to that of the 500 nm masking polystyrene nanospheres. Cracks are formed in these NPGN due to the good adhesion to the substrate via a continuous Au layer underneath. The cracking issue has been resolved by simultaneous Ag leaching and releasing as shown in FIG. 17. To prove the concept, the polystyrene nanospheres were drop-coated without forming a compact layer. Spin coating and oxygen plasma erosion techniques will be employed in the future to produce compact nanosphere mask for high-throughput fabrication. ABL may be used for NPGN with arbitrary shapes. For the alternative approach using ABL, our collaborator (J Wolfe) has successfully fabricated the requisite resist patterns as small as 60 nm diameter (FIG. 23(a)) over 1 in$^2$.

NPGN SERS Mapping:

We have successfully obtained benzenethiol self-assembled monolayer SERS map from un-released NPGN (area 25×25 micron$^2$) as shown in FIG. 18(e). The high quality SERS spectrum in FIG. 1(d) (from 1 micron$^2$ area, 0.2 mW/micron$^2$, 10 sec) has signal level ~$10^5$ higher than that from typical non-porous substrates with known enhancement factor $5*10^5$, as well as published nanoporous Au results, suggesting our NPGN has an enhancement factor ~$10^{10}$. We will measure benzenethiol SERS from NPGN with different thickness to study the thickness-dependent SERS.

Figure 23:
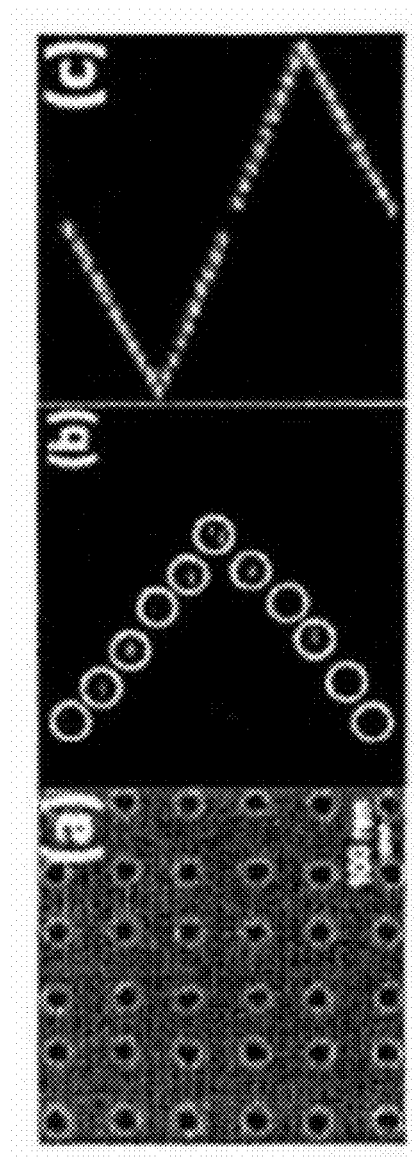
FIGS. 23(a)-(c) show ABL resist pattern of 60 nm circles, 11-spot SERS tracking, and 50-spot Si Raman.
Figure 24:
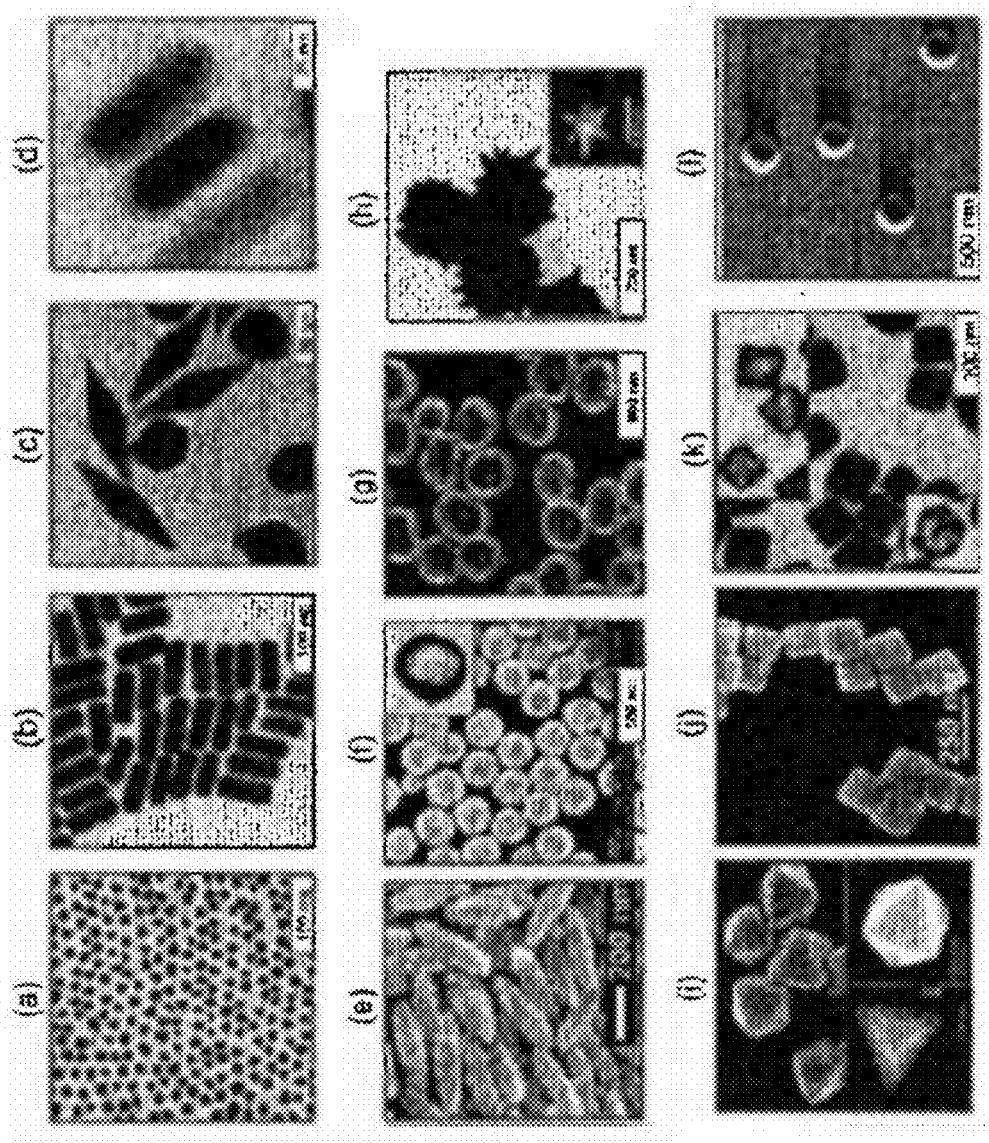
FIGS. 24(a)-(l) show various types of plasmon-resonant nanoparticles: spheres; rods; bipyramids; rods @ Ag shells; rice; shells; bowls; spiky shells; nanostars, tetrahedra, octahedra, and cuboctahedra; cube; cages; and crescents.

NPGN Tracking:

FIG. 23(b) shows the 11-dot monitoring of gold nanoshells simultaneously with the nanoshell coated with benzenethiol SAM. FIG. 23(c) shows simultaneous 50-point Raman acquisition from a silicon wafer.

NPGN as an Ultra-Sensitive Molecular Sensor with Uncooled Detector:

Although SERS is highly sensitive, it requires a cooled detector in virtually all current applications. The primary reason for that is the nanostructure only has a very limited surface area for molecule of interest to attach. Due to the ultra-high surface-to-volume ratio and the strong nanoplasmonic effect, NPGN can be an ultra-sensitive molecular sensor with uncooled detectors. Here, we have measured benzenethiol SAM coated NPGN at 15, 10, 5 and 0° C. detector temperature with signal-to-noise ratio 26.5, 8.5, 5.89, and 3.9, respectively. We expect SNR ~1 at 30° C. The SERS signal is collected from ~4 NPGN units with a total number of molecule ~100 million (or 100 atto mole). The laser intensity is 10 mW/micron$^2$ and the total spectral acquisition time is 20 sec. Spectra are shown in FIG. 16. NPGN could enable ultra-light weight portable SERS meters because only a uncooled CCD chip and a laser pointer like laser is needed.

Multi-modal spectral microscopy may be performed over a population of NPGN in ethanol, water and bacterial cell cultures. In ethanol, the NPGN will be coated with benzenethiol SAM and then imaged under wet and dry conditions. For the dry experiment, a line-scan confocal Raman microscope will be employed to generate a SERS map over a large area (100×100 μm2). In the wet experiment, a 3D multi-point SERS nanoparticle tracking system recently developed will be used. These measurements will allow us to identify the wavelength of surface plasmon resonance and obtain the NPGN SERS brightness. In the water and cell culture experiments, the NPGN will be infused with photosensitizer indocyanine green (ICG) and subsequently protected by thiol-polyethyleneglycol (T-PEG) to prevent NPGN aggregation. The line-scan and 3D tracking systems mentioned earlier will be employed to assess the SERS-based imaging capability of NPGN. The NPGNs are not expected to be internalized by the bacterial cells. Next, we will assess the photothermal effect of NPGN by using an external NIR source for heating. Photothermal effects will be assessed by the NPGN SERS and the intensity of infused ICG fluorescence simultaneously. We expect to observe ICG SERS only from the NPGN due to its plasmonic enhancement, whereas, we could observe ICG fluorescence from the NPGN depending on the degree of plasmonic fluorescence quenching. In contrast, the released ICG can be quantified by observing a negative correlation between ICG fluorescence from the external microenvironment of the NPGN and the ICG SERS from the NPGN. Localized heating will also be assessed using thermally sensitive dyes, such as Leuco, and by direct measurement using a thermal couple probe on the sample. Once the ICG release exceeds a threshold, photodynamic effects will be assessed by a singlet oxygen fluorescence marker (e.g. Sensor Green, ex/ex ~504/525 nm, Invitrogen) using a separate excitation/emission channel of the microscope.

Those with ordinary skill in the art will recognize that the disclosed embodiments have relevance to a wide variety of areas in addition to those specific examples described above.

The foregoing description of the exemplary embodiments is provided to enable any person skilled in the art to make and use the claimed subject matter. Various modifications to these embodiments will be readily apparent to those skilled in the art, and the generic principles defined herein may be applied to other embodiments without the use of the innovative faculty. Thus, the claimed subject matter is not intended to be limited to the embodiments shown herein but is to be accorded the widest scope consistent with the principles and novel features disclosed herein.

It is intended that all such additional systems, methods, features, and advantages that are included within this description be within the scope of the claims.

What is claimed is:

1. A nanoporous gold structure comprising:
   a plurality of nanoporous gold discs, each nanoporous gold disc comprising:
   a substrate layer;
   an adhesion layer disposed in association with the substrate layer; and
   a porous gold layer disposed in association with the adhesion layer, wherein the porous gold layer comprises a nanoporous 3-dimensional network of pores extending throughout the porous gold layer's entire volume and is adapted for adsorbing and releasing molecules into and from the pores thereof, wherein the pores in the porous gold layer have a width ranging from about 5 nanometers to about 20 nanometers, and wherein the nanoporous gold structure has a red-shifted plasmon resonance peak of at least 650 nm.

2. The structure of claim 1, wherein the substrate comprises silicon.

3. The structure of claim 1, wherein the adhesion layer comprises gold, chromium, or combinations thereof.

4. The structure of claim 1, wherein the porous gold layer further comprises silver.

5. The structure of claim 1, wherein the porous gold layer has a thickness ranging from 50 nanometers to 1000 nanometers.

6. The structure of claim 1, wherein the adhesion layer has a thickness of approximately 65 nanometers.

7. The structure of claim 1, wherein the porous gold layer is at least partially transparent.

8. The structure of claim 1, further comprising molecules bound to surfaces of the pores of the nanoporous network, wherein the molecules comprise protein, DNA, RNA, a pharmacologically active substance, or combinations thereof.

9. A nanoporous gold structure comprising:
a plurality of nanoporous gold discs, each nanoporous gold disc comprising:
a substrate layer; and
a porous gold layer disposed in association with the substrate layer, wherein the porous gold layer comprises a nanoporous 3-dimensional network of pores extending throughout the porous gold layer's entire volume and is adapted for adsorbing and releasing molecules into and from the pores thereof, wherein the pores in the porous gold layer have a width ranging from about 5 nanometers to about 20 nanometers, and wherein the nanoporous gold structure has a red-shifted plasmon resonance peak of at least 650 nm.

10. The structure of claim 9, further comprising an adhesion layer disposed in association with the substrate layer, wherein at least a portion of the porous alloy layer is disposed in association with the adhesion layer.

11. The structure of claim 10, wherein the adhesion layer comprises gold, chromium, or combinations thereof.

12. The structure of claim 9, wherein the substrate comprises silicon.

13. The structure of claim 9, wherein the porous gold layer further comprises silver.

* * * * *